US010653700B2

(12) United States Patent
Hsu

(10) Patent No.: US 10,653,700 B2
(45) Date of Patent: May 19, 2020

(54) COMPOSITION COMPRISING A THERAPEUTIC AGENT AND A RESPIRATORY STIMULANT AND METHODS FOR THE USE THEREOF

(71) Applicant: John Hsu, Rowland Heights, CA (US)

(72) Inventor: John Hsu, Rowland Heights, CA (US)

( * ) Notice: Subject to any disclaimer, the term of this patent is extended or adjusted under 35 U.S.C. 154(b) by 0 days.

(21) Appl. No.: 16/001,711

(22) Filed: Jun. 6, 2018

(65) Prior Publication Data

US 2018/0296565 A1 Oct. 18, 2018

Related U.S. Application Data

(63) Continuation of application No. 15/214,421, filed on Jul. 19, 2016, now Pat. No. 10,004,749.

(60) Provisional application No. 62/195,769, filed on Jul. 22, 2015, provisional application No. 62/523,217, filed on Jun. 21, 2017.

(51) Int. Cl.
*A61K 31/5377* (2006.01)
*A61K 31/485* (2006.01)
*A61K 9/00* (2006.01)
*A61K 9/20* (2006.01)
*A61K 9/24* (2006.01)
*A61K 9/50* (2006.01)
*A61K 45/06* (2006.01)

(52) U.S. Cl.
CPC ........ *A61K 31/5377* (2013.01); *A61K 9/0019* (2013.01); *A61K 9/0053* (2013.01); *A61K 9/209* (2013.01); *A61K 9/2054* (2013.01); *A61K 9/5047* (2013.01); *A61K 9/5073* (2013.01); *A61K 31/485* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2002/0010127 A1* | 1/2002 | Oshlack | ............... | A61K 9/0031 424/449 |
| 2003/0092701 A1* | 5/2003 | Lalley | ................ | A61K 31/4745 514/217.02 |
| 2012/0270848 A1* | 10/2012 | Mannion | ............ | A61K 31/5377 514/171 |
| 2014/0030322 A1 | 1/2014 | Bosse et al. | | |

OTHER PUBLICATIONS

Sullivan Ma et al: "Buprenorphine/naloxone for the treatment of prescription opioid abuse and chronic pain", Drug and Alcohol Dependence, vol. 140, 2014.
P. A. Flecknell et al: "Reversal of fentanyl/fluanisone neuroleptanalgesia in the rabbit using mixed agonist/antagonist opioids", Laboratory Animals., vol. 23, No. 2, Apr. 1, 1989.
Extended European Search Report, dated May 10, 2019.
European Written Opinion dated May 10, 2019.

\* cited by examiner

*Primary Examiner* — Bethany P Barham
*Assistant Examiner* — Barbara S Frazier
(74) *Attorney, Agent, or Firm* — Entralta PC; James F. Fleming; Peter D. Weinstein

(57) ABSTRACT

The present disclosure provides a safe method for anesthesia or the treatment of pain by safely administering an amount of active agent to a patient while reducing the incidence or severity of suppressed respiration. The present disclosure provides a pharmaceutical composition comprising a therapeutic agent and a chemoreceptor respiratory stimulant. In one aspect, the compositions oppose effects of respiratory suppressants by combining a chemoreceptor respiratory stimulant with an opioid receptor agonist or other respiratory-depressing drug. The combination of the two chemical agents, that is, the therapeutic agent and the respiratory stimulant, may be herein described as the "drugs." The present compositions may be used to treat acute and chronic pain, sleep apnea, and other conditions, leaving only non-lethal side effects.

13 Claims, No Drawings

COMPOSITION COMPRISING A THERAPEUTIC AGENT AND A RESPIRATORY STIMULANT AND METHODS FOR THE USE THEREOF

RELATED APPLICATIONS

This is a continuation application and so claims the benefit pursuant to 35 U.S.C. § 120 of a prior filed and co-pending U.S. non-provisional patent application Ser. No. 15/214,421 filed Jul. 19, 2016, and entitled "Composition comprising a therapeutic agent and a respiratory stimulant and methods of use thereof", which itself claims priority pursuant to 35 U.S.C. § 119(e) to and is entitled to the filing date of U.S. provisional patent application Ser. No. 62/195,769 filed Jul. 22, 2015, and entitled "Composition comprising a therapeutic agent and a respiratory stimulant and methods of use thereof". The contents of the aforementioned application(s) are incorporated herein by reference.

BACKGROUND OF THE INVENTION

Certain pharmaceutical drugs are known to suppress respiration. Of those pharmaceutical drugs, opioid receptor agonists (also described herein as either "opioids" or "narcotics") are the most well-known.

Most often, opioids are currently used to treat pain. Opioids are potent analgesics and they are prescribed for patients in pain who need powerful painkillers. Acute pain, (for example, pain in duration of less than three months), is treated most often with short acting immediate release opioid medications, while chronic pain, (for example, pain in duration of greater than three months), is treated often with long acting or extended release formulations of opioid medications.

Chronic nonmalignant pain is a silent epidemic in the U.S. that affects approximately 116 million Americans. Patients who take opioids for an extended period, can develop a tolerance and require higher and higher doses of the drugs, increasing the risk of overdose and other problems. It is also the most common reason patients seek medical care, resulting in $635 billion annually in both medical costs and decreased work productivity. Although the physiology of chronic pain continues to be poorly understood, it has been identified as a disorder associated with many psychosocial conditions, including lack of appetite, depression, and sleep disturbances.

Opioids have well-known pharmacodynamic profiles associated with a significant number of side effects and complications. Common side effects of opioid administration include sedation, dizziness, nausea, vomiting, and constipation. Less common side effects may include delayed gastric emptying, hyperalgesia, immunologic and hormonal dysfunction, infertility, muscle rigidity, myoclonus, physical dependence, tolerance, respiratory depression, respiratory arrest and death. Painkiller deaths quadrupled between 1999 and 2011, mirroring a sharp rise in the number of prescriptions for such drugs. In 2009, overdoses involving painkillers pushed drug fatalities past traffic accidents as a cause of death. In 2011 the U.S. Centers for Disease Control and Prevention declared prescription opioid abuse an epidemic.

Well-known complications of opioids include the phenomenon of both physical and psychological dependence and addiction, which can in turn lead to opioid misuse, abuse and diversion. More than 70% of the illegal users obtain opioids by stealing them during pharmacy robberies, purchasing them illegally on the black market, or receiving them from family or friends. These individuals seek to achieve a "high" from prescription medications by taking an excess number of pills orally or by crushing the pills, followed by snorting, smoking, or injecting the new altered formulation. The misuse or abuse of prescription opioid medications is a growing problem, with abuse rates having quadrupled in the decade from 1990 to 2000. The deaths associated with abuse and misuse of prescription pain drugs have also quadrupled between 1999 and 2011. Frequently death associated with the overdose of opioids occurs within an hour of the administration of the opioid due to respiratory suppression.

Because the availability of opioids has increased, there are now more deaths and overdoses from prescription opioids than deaths from heroin overdoses. A study published in the November 2014 issue of the journal Pain found an increased risk of death associated in patients with chronic pain prescribed opioids for long-term use while a somewhat lower risk was associated with short-term use.

The increased availability of opioids was partially brought about by The Joint Commission On Accreditation of Healthcare Organizations (JCAHO) standards from 2000 that demands pain be addressed by healthcare providers as the fifth vital sign. The evaluation of pain was thus made equivalent to the evaluation of a patient's vital signs including the heartbeat, blood pressure, respiratory rate, and temperature. A 2012 study showed that physicians played an important role in prescription drug overdoses as they attempted to comply with Federal mandates, avoid malpractice claims, avoid decreased patient satisfaction scores (as patients began demanding more prescriptions for opioid pain medications), and avoid decreased reimbursement. The same study found that of 3,733 fatalities associated with prescription opioid drugs, the drugs that caused or contributed to nearly half of the deaths were prescribed to patients by physicians. This public health issue confounds the clinical utility of opioids. The extent of their efficacy in the treatment of pain when utilized on a chronic basis has not been definitively proven and has made long-term treatment of non-cancer pain with opioids controversial. Coupled with the abuse and addiction potential, clinical safety concerns and side effect profile, proper physician prescribing of opioids may be prevented, and result in inadequate pain management.

Though the bulk of the current research is focused on abuse deterrence, addiction avoidance and patient safety, prescription drug are still abused, overdoses occur and death rates continue to rise. It is apparent that this approach is not successful in preventing patient deaths. The abuse deterrent developments have either been too difficult to manufacture or fail in clinical use. "Mu receptor Modulation" has not worked. A different approach must to be tried to save patient lives. Presently, as abuse deterrence technologies are developed, narcotic abusers and addicts quickly discover innovative methods to achieve their goal of reaching a euphoric "high". They crush drugs, intravenously inject drugs, snort drugs, extract drugs with alcohol or combine multiple drugs to defeat pharmaceutical abuse deterrence technology as they are developed. It is a cycle that has led to many deaths. The CDC determined that abuse of prescription opioid drugs is an epidemic because it has led to a quadrupling of death rates in recent years. Rethinking of the method in which pain is treated with opioids must be done. The current trend to use multimodal pain therapy, which utilizes non-narcotics in synergy to treat pain is a step in the right direction. Unfortunately, in clinical practice this has been implemented by only about 30 percent of physicians in the country. Rethinking of the method in which opioids are used to treat pain must also be done. There is an epidemic of prescription drug abuse and it is getting worse despite efforts to solve it. More opioid pain medications are prescribed today than ever before because of Federal JCAHO regulations mandating the treatment of pain. The pharmaceutical industry's attempts to develop effective abuse deterrent solutions have largely been unsuccessful. And even though the Federal government regulations including REMS (Risk Evaluation and Mitigation Strategies), CURES (Controlled Substance Review Evaluation System), and ETASU (Elements to Assure Safe Use) regulations to restrict prescribing practices for opioid use have been implemented, deaths from overdose still occurs.

Progressive and ultimately life-threatening respiratory events may go unrecognized until significant morbidity or mortality occurs. Drug-induced respiratory depression (DIRD) is a common problem with opioid use. It is not always possible to predict the timing or severity of DIRD due to the number of contributing factors. To illustrate, among postoperative patients receiving opioids, the incidence of clinically significant respiratory depression (respiratory acidosis and hypoxemia) requiring intervention occurs in approximately 2% of the surgical population. Unfortunately, it is not always possible to predict the timing or severity of these events due to the number of contributing factors, including age, sex, body-mass index, presence of co-morbidities, and concomitant medications administered. On the other hand, some risk factors are very strong predictors of respiratory complications post-operatively. For example, in bariatric patients the incidence of deleterious respiratory events post-operatively may be as high as 100%. Typically, in the immediate post-operative period and while in the post-anesthesia care unit, a patient's ventilatory performance is monitored intensively and respiratory depression can be treated early with interventions such as verbal stimulation, oxygen therapy, and positive airway pressure (i.e., CPAP). Occasionally, profound respiratory depression requires reversal by administering a selective antagonist of naloxone or flumazenil, and/or decreasing subsequent doses of the depressant agent. Although this approach may improve respiratory function, sedation and/or analgesia will be sub-optimal. If a safe and effective respiratory stimulant drug were available to support breathing post-operatively it is likely that pain control in some patients would improve because analgesia could be used as the endpoint for titration of an opioid rather than the magnitude of respiratory depression it elicits. A safe and effective respiratory stimulant could improve patient care by avoiding the use of opioid reversal agents (e.g., naloxone, which reverses analgesia as well as respiratory depression) thereby permitting better pain management by enabling the use of higher doses of analgesics. Thus, there is a need for a respiratory stimulant beyond the post-anesthesia care unit.

A novel new pain medication could break the cycle whereby addicts who continue to abuse opioids do not die, and the use of opioids becomes a safer option.

In view of the consequences of increased opioid prescription and/or administration there is an apparent unmet need for a safe method of treating pain, which adequately addresses the pain levels of acute and/or chronic pain sufferers yet also decreases the risk of overdose by pain medications. Further, in view of the consequences of patient tolerance to increased levels of analgesics, there is a need to safely administer high doses of active agents to the patients, while avoiding the side effects which lead to death, such as respiratory suppression.

SUMMARY OF THE INVENTION

Aspects of the present specification disclose a pharmaceutical composition comprising a therapeutic agent and a respiratory stimulant. The therapeutic agent disclosed herein may be an analgesic, a benzodiazepine, a barbiturate, an antihistamine, or pharmaceutically acceptable salts thereof, and any combination thereof. An analgesic disclosed herein may be an opioid receptor agonist (an opioid) or a non-steroidal anti-inflammatory agent or NSAID. Opioid receptor agonists include mu and kappa receptor agonists. A respiratory stimulant disclosed herein may be doxapram, modafinil, almitrine, AMPAkines, GAL-021, buspirone, mosapride, CX546, CX717, pharmaceutically acceptable salts thereof, or any combination thereof.

In one aspect, the invention is a pharmaceutical composition comprising a respiratory stimulant selected from the group consisting of doxapram and modafinil and a therapeutic agent selected from the group consisting of hydrocodone, oxycodone, hydromorphone, lorazepam, alprazolam, carisprodol, and methocarbamol.

In one aspect, the invention is a pharmaceutical composition comprising a respiratory stimulant doxapram and a therapeutic agent selected from the group consisting of hydrocodone, oxycodone, hydromorphone, lorazepam, alprazolam, carisprodol, and methocarbamol. In another aspect, the respiratory stimulant is modafinil and the therapeutic agent is selected from the group consisting of hydrocodone, oxycodone, hydromorphone, lorazepam, alprazolam, carisprodol, and methocarbamol.

Aspects of the present specification disclose an oral dosage form comprising a pharmaceutical composition disclosed herein. An oral dosage form disclosed herein may be a syrup, a tablet, a caplet, a gelcap, a lozenge, or a capsule.

Aspects of the present specification disclose a method of administering anesthesia. Aspects of this method comprising administering a pharmaceutical composition disclosed herein or an oral dosage form disclosed herein to a patient in need thereof.

DETAILED DESCRIPTION OF THE INVENTION

It is an object is to provide a safe method for anesthesia or the treatment of pain. It is a further object is to safely administer an increased amount of active agent to a patient while reducing the incidence or severity of suppressed respiration. The above objects and others are attained by the disclosed pharmaceutical compositions comprising a therapeutic agent and a chemoreceptor respiratory stimulant. It is a focus of this project to establish a novel pain medication to oppose opioid respiratory effects by compounding (combining) a chemoreceptor respiratory stimulant with an opioid receptor agonist or other respiratory-depressing drug. The combination of the two chemical agents, that is, the therapeutic agent and the respiratory stimulant, may be herein described as the "drugs." This novel pain medication can be employed to treat acute and chronic pain whereby the issue of mortality is removed, leaving only nonlethal side effects. It can be considered a "functional antagonism".

In one embodiment, this novel pain medication can be employed to treat acute and chronic pain whereby the issue of mortality is removed, leaving only non-lethal side effects. It would, in one non-limiting example, combine hydrocodone with a chemoreceptor respiratory stimulant.

A therapeutic agent or active agent: As used herein, the phrase "therapeutic agent" refers to a pharmaceutical agent that causes a biological effect when a sufficient amount is absorbed into the blood stream of a patient. In one embodiment, the therapeutic agent is a barbiturate, a benzodiazepine, an antihistamine, an analgesic, or other central nervous system depressant.

In one aspect the therapeutic agent is a barbiturate. The barbiturate can be short and intermediate acting or long acting, e.g., allobarbital, alphenal, aprobarbital, brallobarbital, cyclobarbital, methylpehnobarbital, talbutal, thiamylal, methohexital (BREVITAL®), thiamyl (SURITAL®), thiopental (PENTOTHAL®), amobarbital (AMYTAL®), pentobarbital (NEMBUTAL®), secobarbital (SECONAL®), butalbital (FIORINA®), butabarbital (BUTISOL®), phenobarbital (LUMINAL®), and mephobarbital (MEBARAL®).

In one aspect, the therapeutic agent is a benzodiazepine. In this aspect, the benzodiazepine may be, e.g., alprazolam (sold as HELEX™, XANAX™, XANOR™, ONAX™, ALPROX™, RESTYL™, TAFIL™); Bentazepam (sold as THISDIPONA™); bretazenil, bromazepam (sold as LECTOPAM™, LEXAURIN™, LEXOTANIL™, LEXOTAN™, BROMAN™); brotizolam (sold as LENDORMIN™, DORMEX™, SINTONAL™, NOCTILAN™); camazepam (sold as ALBEGO™, LIMPIDON™, PAXOR™); chlordiazepoxide (sold as LIBRIUM™, RISOLID™, ELANIUM™); cinolazepam (sold as GERODORM™); clobazam (sold as Frisium™, URBANOL™); clonazepam (sold as RIVATRIL™, RIVOTRIL™, KLONOPIN™, IKTOROVIL™, PAXAM™); clorazepate (sold as TRANXENE™, TRANXILIUM™); clotiazepam (sold as VERATRAN™, CLOZAN™, RIZE™); cloxazolam (sold as SEPAZON™, OLCADIL™); delorazepam (sold as DADUMIR™); deschloroetizolam (sold as THIALPRAZOLAM™); diazepam (sold as ANTENEX™, APAURIN™, APZEPAM™, APOZEPAM™, HEXALID™, PAX™, STESOLID™, STEDON™, VALIUM™, VIVAL™, VALAXONA™); diclazepam; estazolam (sold as PROSOM™); ethyl carfluzepate; etizolam (sold as ETILAAM™, ETIZEST™, PASADEN™, DEPAS™); ethyl loflazepate (sold as VICTAN™, MEILAX™, RONLAX™); flubromazepam; flunitrazepam (sold as ROHYPNOL™, HIPNOSEDON™, VULBEGAL™, FLUSCAND™, FLUNIPAM™, RONAL™, ROHYDORM™); flurazepam (sold as DALMADORM™, DALMANE™); flutoprazepam (sold as RESTAS™); halazepam (sold as PAXIPAM™); ketazolam (sold as ANXON™); loprazolam (sold as DORMONOCT™); lorazepam (sold as ATIVAN™, LORENIN™, LORSILAN™, TEMESTA™, TAVOR™, LORABENZ™); lormetazepam (sold AS LORAMET™, NOCTAMID™, PRONOCTAN™); medazepam (sold as NOBRIUM™, ANSILAN™, MEZAPAM™, RUDOTEL™, RAPORAN™); midazolam (sold as DORMICUM™, VERSED™, HYPNOVEL™, DORMONID™); nimetazepam (sold as ERIMIN™); nitrazepam (sold as MOGADON™, ALODORM™, PACISYN™, DUMOLID™, NITRAZADON™); nordiazepam (sold as MADAR™, STILNY™); oxazepam (sold as SERESTA™, SERAX™, SERENID™, SEREPAX™, SOBRIL™, OXABENZ™, OXAPAX™, OPAMOX™); phenazepam; pinazepam (sold as DOMAR™); prazepam (sold as LYSANXIA™, CENTRAX™); premazepam; pyrazolam (sold as PYRAZOLAM™, BROMAZOLAM™); quazepam (sold as DORAL™); temazepam (sold as RESTORIL™, NORMISON™, EUHYPNOS™, TEMAZE™, TENOX™); tetrazepam (sold as MYOLASTAN™); triazolam (sold as HALCION™, RILAMIR™); flumazenil (sold as ANEXATE™, LANEXAT™, MAZICON™, ROMAZICON™); eszopiclone (sold as LUNESTA™); zaleplon (sold as SONATA™, STARNOC™); zolpidem (sold as AMBIEN™, NYTAMEL™, SANVAL™, STILNOCT™, STILNOX™, SUBLINOX™ (Canada), XOLNOX™, ZOLDEM™, ZOLNOD™); or zopiclone (sold as IMOVANE™, RHOVANE™, XIMOVAN™; ZILEZE™; ZIMOCLONE™; ZIMOVANE™; ZOPITAN™; ZORCLONE™).

In yet another aspect, the therapeutically active agent is an antihistamine. Antihistamines are known in the art, and a non-limiting list of antihistamines includes: acrivastine, azelastine, bilastine, brompheniramine, buclizine, bromodiphenhydramine, carbinoxamine, cetirizine (ZYRTEC™; metabolite of hydroxyzine, its prodrug), chlorpromazine, cyclizine, chlorphenamine, chlorodiphenhydramine, clemastine, cyproheptadine, desloratadine, dexbrompheniramine, dexchlorpheniramine, dimenhydrinate, dimetindene, diphenhydramine (BENADRYL™), doxylamine, ebastine, embramine, fexofenadine (ALLEGRA™), hydroxyzine (VISTARIL™), levocetirizine, loratadine (CLARITIN™), meclozine, mirtazapine, olopatadine, orphenadrin, phenindamine, pheniramine, phenyltoloxamine, promethazine, pyrilamine, quetiapine (SEROQUEL™), rupatadine, tripelennamine, triprolidine, cimetidine, famotidine, lafutidine, nizatidine, ranitidine, roxatidine, tiotidine, mixtures thereof, and pharmaceutically acceptable salts thereof. In another aspect, the therapeutically active agent is an analgesic. The analgesic may be an opioid receptor agonist (also called an opioid), or a non-steroidal anti-inflammatory agent. In one aspect of this embodiment, the opioid receptor agonist is the opioid mu receptor agonist or a opioid kappa receptor agonist.

In another aspect, the opioid receptor agonist is, e.g., alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydroetorphine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levallorphan, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propiram, propoxyphene, propylhexedrine, sufentanil, tilidine, tramadol, pharmaceutically acceptable salts of any of the foregoing, and mixtures of any two or more of the foregoing.

In another aspect of the invention, the opioid receptor agonist is a opioid mu receptor agonist that may be, e.g., DAMGO ([D-Ala2, NMe-Phe4, Gly-ol5]-enkephalin), Endomorphin-1 (Endomorphin-1 Tyr-Pro-Trp-Phe-NH2), Endomorphin-2 (Tyr-Pro-Phe-Phe-NH2), Fentanyl citrate (N-Phenyl-N-[1-(2-phenylethyl)-4piperidinyl]propanamide citrate), loperamide hydrochloride (4-(4-Chlorophenyl)-4-hydroxy-N,Ndimethyl-α,α-diphenyl-1-piperidinebutanamide hydrochloride), metazinol hydrochloride (3-(3Ethylhexahydro-1-methyl-1H-azepin-3-yl)phenol hydrochloride), oxycodone hydrochloride ((5α)4,5-Epoxy-14-hydroxy-3-methoxy-17-methylmorphinan-6-one hydrochloride), PL 017 (Tyr-ProN-Methyl-Phe-D-Pro-NH2), or sinomenine hydrochloride (9α,13α,14α-7,8-Didehydro-4-hydroxy3,7-dimethoxy-17-methylmorphinan-6-one hydrochloride).

In another aspect, the opioid receptor agonist is the opioid kappa receptor agonist, e.g., 6'-Guanidinonaltrindole (6'-GNTI)—biased ligand: G protein agonist, β-arrestin antagonist, 8-Carboxamidocyclazocine, Alazocine—partial agonist, Asimadoline—peripherally-selective, Bremazocine—highly selective, Butorphan—full agonist, Butorphanol—partial agonist, BRL-52537, CR665—peripherally-selective, Cyclazocine—partial agonist, Cyclorphan full agonist, Difelikefalin (CR845)—peripherally-selective, Diprenorphine—non-selective; partial agonist, Dynorphins (dynorphin A, dynorphin B,big dynorphin)—endogenous peptides, Eluxadoline, Enadoline, Erinacine E, Etorphine, GR-89696—selective for κ2, HS665, HZ-2, Ibogaine—naturally-occurring, ICI-204,448—peripherally-selective, ICI-199,441, Ketamine, Ketazocine, Levallorphan, Levomethorphan, Levorphanol, LPK-26—highly selective, MB-1C—OH, Menthol—naturally-occurring, Metazocine—partial agonist, Morphine—naturally-occurring, N-MPPP, Nalbuphine—partial agonist, Nalfurafine—full agonist; atypical agonist (possibly biased or subtype-selective), Nalmefene—partial agonist, Nalodeine, Nalorphine—partial agonist, Niravoline, Norbuprenorphine—partial agonist; peripherally-selective metabolite of buprenorphine, Norbuprenorphine-3-glucuronide—likely partial agonist; peripherally-selective metabolite of buprenorphine, Noribogaine—non-selective; naturally-occurring; biased ligand: G protein agonist, β-arrestin antagonist, Oxilorphan—partial agonist, Oxycodone—selective for κ2bsubtype, Pentazocine—partial agonist, Phenazocine—partial agonist, Proxorphan—partial agonist, RB-64 (22-thiocyanatosalvinorin A)—G protein biased agonist with a bias factor of 96; β-arrestin antagonist, Salvinorin A—naturally-occurring, 2-Methoxymethyl salvinorin B[38]—and its ethoxymethyl and fluoroethoxymethyl homologues, Samidorphan—nonselective; weak partial agonist, Spiradoline, Tifluadom, U-50,488, U-54,494A, U-69,593, Xorphanol—partial agonist, Nalfurafine (Remitch), which was introduced in 2009, is the first selective KOR agonist to enter clinical use.

In another aspect, the non-steroidal anti-inflammatory agent is acetylsalicylic acid (aspirin), celecoxib (CELEBREX™), dexdetoprofen (KERAL™), diclofenac (VOLTAREN™, CATAFLAM™, VOLTAREN-XR™), diflunisal (DOLOBID™), etodolac (LODINE™, LODINE XL™), etoricoxib (ALGIX™), fenoprofen (FENOPRON™, NALFRON™), firocoxib (EQUIOXX™ PREVICOX™), flurbiprofen (URBIFEN™, ANSAID™, FLURWOOD™, FROBEN™), ibuprofen (ADVIL™, BRUFEN™, MOTRIN™, NUROFEN™, MEDIPREN™, NUPRIN™), indomethacin (INDOCIN™, INDOCIN SR™, INDOCIN IV™), ketoprofen (ACTRON™, ORUDIS™ ORUVAIL™, KETOFLAM™), ketorolac (TORADOL™, SPRIX™, TORADOL IV/IM™, TORADOL IM™). licofelone, lornoxicam (XEFO™), loxoprofen (LOXONIN™, LOXOMAC™, OXENO™), lumiracoxib (PREXIGE™), meclofenamic acid (MECLOMEN™), mefenamic acid (PONSTEL™), meloxicam (MOVALIS™, MELOX™, RECOXA™, MOBIC™), nabumetone (RELAFEN™), naproxen (ALEVE™, ANAPROX™, MIDOL EXTENDED RELIEF™ NAPROSYN™, NAPRELAN™), nimesulide (SULIDE™, NIMALOX™, MESULID™), oxaporozin (DAYPRO™, DAYRUN™, DURAPROX™), parecoxib (DYNASTAT™), piroxicam (FELDENE™), rofecoxib (VIOXX™, CEOXX™, CEEOXX™), salsalate (MONOGESIC™, SALFLEX™, DISALCID™, SALSITAB™), sulindac (CLINORIL™), tenoxicam (MOBIFLEX™), tolfenamic acid (CLOTAM RAPID™, TUFNIL™), and valdecoxib (BEXTRA™).

As used herein, the phrase "pharmaceutically acceptable salt," refers to a salt formed from an acid and the basic nitrogen group of a therapeutic agent. Preferred salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, urinate, pantothenate, bitartrate, ascorbate, succinate, maleate, gentisinate, fumarate, gluconate, glucaronate, saccharate, formate, benzoate, glutamate, methanesulfonate. ethanesulfonate, benzenesulfonate, p-toluenesulfonate, and pamoate (i.e., 1,1'-methylene-bis(2-hydroxy-3-naphthoate)) salts.

The term "pharmaceutically acceptable salt" also refers to a salt prepared from a therapeutic agents having an acidic functional group, such as a carboxylic acid or sulfonic acid functional group, and a pharmaceutically acceptable inorganic or organic base. Suitable bases include, but are not limited to, hydroxides of alkali metals such as sodium, potassium, cesium and lithium; hydroxides of alkaline earth metal such as calcium and magnesium; hydroxides of other metals, such as aluminum and zinc; ammonia, and organic amines, such as unsubstituted or hydroxysubstituted mono-, di-, or trialkylamines; dicyclohexylamine; tributyl amine; pyridine; N-methyl,Nethylamine; diethylamine; triemylamine; mono-, bis-, or tris-(2-hydroxy-lower alkyl amines), such as mono-, bis-, or tris-(2-hydroxyethyl)amine, 2-hydroxy-tert-butylamine, or tris(hydroxymethyl)methylamine, N,N-di-lower alkyl-N-(hydroxy lower alkyl)-amines, such as N,N,dimethyl-N-(2-hydroxyethyl)amine, or tri-(2-hydroxyethyl)amine; N-methyl-D-glucamine; N,N'dibenzylemylenediamine, triethanolamine; inorganic acid salts such as hydrochloride, hydrobomide; organic acid salts such as formate, acetate, trifluoroacetate; and amino acids such as arginine, lysine, asparginate, glutamate and the like. In a particular embodiment, the therapeutic agent is hydrocodone. Hydrocodone is the most frequently prescribed opioid in the United States and is associated with more drug abuse and diversion than any other licit or illicit opioid. It is an orally active agent most frequently prescribed for the treatment of moderate to moderately severe pain. Its analgesic potency is similar to morphine. Hydrocodone is also an antitussive (cough suppressant) agent with an efficacy similar to that of codeine. There are numerous brand and generic hydrocodone products marketed in the United States. All are combination products. The most frequently prescribed combination is hydrocodone and acetaminophen (for example, VICODIN®, LORCET®, NORCO™ and LORTAB®). Other examples of combination products include those containing aspirin (LORTAB® ASA), ibuprofen (VICOPROFEN®), and antihistamines (HYCOMINE®). The street names for these are Hydro, Norco, and Vikes, respectively. Hydrocodone has a chemical structure that is related to that of codeine and morphine. Hydrocodone combination products are formulated in tablets, capsules, and syrups. The methods of Hydrocodone abuse is most often by oral rather than intravenous administration. Hydrocodone, like most other opioids, induces euphoria, sedation and alters the perception of painful stimuli. Its effect on body includes drowsiness, dizziness, nausea, constipation, urinary retention and in higher amounts, depressed respiration and death. Long term use can lead to dependence and addiction. Withdrawal symptoms include restlessness, muscle and bone pain, insomnia, diarrhea, and vomiting. The drugs with similar effects include morphine, heroin, oxycodone, codeine, propoxyphene, fentanyl, and hydromorphone. The overdose effects include, like other opioids, cold and clammy skin, severely constricted pupils, and slow breathing that can lead to a loss of consciousness and death. Large doses of hydrocodone in combination with acetaminophen may cause severe liver damage.

The legal status of hydrocodone in the United States has recently changed in 2014. Hydrocodone is now a Schedule II narcotic. Schedule III drug products have accepted medical use in treatment and have a moderate to low physical dependence or high psychological dependence. As of 2006, hydrocodone was the active antitussive in more than 200 formulations of cough syrups and tablets sold in the United States. In late 2006, the U.S. Food and Drug Administration (FDA) began forcing the recall of many of these formulations due to reports of deaths in infants and children under the age of six. The legal status of drug formulations originally sold between 1938 and 1962—before FDA approval was required—was ambiguous. As a result of FDA enforcement action, by August 2010, 88% of the hydrocodone containing medications had been removed from the market. As a result, doctors, pharmacists, and codeine-sensitive or allergic patients or sensitive to the amounts of histamine released by its metabolites had to choose among rapidly dwindling supplies of the HYCODAN™ CODICLEAR™ and HYDROMET™ type syrups, TUSSIONEX™—an extended-release suspension similar to the European products CODIPERTUSSIN™ (codeine hydrochloride), PARACODIN™ suspension (dihydrocodeine hydroiodide), TUSSCODIN™ (nicocodeine hydrochloride) and others— and a handful of weak dihydrocodeine syrups. The low sales volume and Schedule II status of dilaudid cough syrup predictably leads to under-utilization of the drug. There are several conflicting views concerning the US availability of cough preparations containing ethylmorphine (also called dionine or codethyline)—FECO SYRUP™ and its equivalents were first marketed circa 1895 and still in common use in the 1940s and 1950s, and the main ingredient is treated like codeine under the Controlled Substances Act of 1970.

As of July 2010, the FDA was considering banning some hydrocodone and oxycodone fixed-combination proprietary prescription drugs—based on the paracetamol content and the widespread occurrence of liver damage. FDA action on this suggestion would ostensibly also affect codeine and dihydrocodeine products such as the TYLENOL™ with codeine and PANLOR™ series of drugs. In 2010, it was the most prescribed drug in the USA, with 131.2 million prescriptions of hydrocodone (combined with paracetamol) being written. Hydrocodone can be habit-forming, causing physical and psychological dependence. Its abuse liability is similar to morphine and less than oxycodone.

Patients consuming alcohol, other opioids, antihistamines, anti-psychotics, anti-anxiety agents, or other central nervous system (CNS) depressants together with hydrocodone may exhibit an additive CNS depression. Hydrocodone may interact with serotonergic medications.

As a narcotic, hydrocodone relieves pain by binding to opioid receptors in the CNS. It acts primarily on μ-opioid receptors, with about six times lesser affinity to δ-opioid receptors. In blood, 20-50% of hydrocodone is bound to protein. Studies have shown hydrocodone is stronger than codeine but only one-tenth as potent as morphine at binding to receptors and reported to be only 59% as potent as morphine in analgesic properties. However, in tests conducted on rhesus monkeys, the analgesic potency of hydrocodone was actually higher than morphine. Hydrocodone has a mean equivalent daily dosage (MEDD) factor of 0.4, meaning that 1 mg of hydrocodone is equivalent to 0.4 mg of intravenous morphine. However, because of morphine's low oral bioavailability, there is a 1:1 correspondence between orally administered morphine and orally administered hydrocodone. The relative milligram strength of hydrocodone to codeine is given as 6 fold, that is, 5 mg has the effect of 30 mg of codeine; by way of the Roman numeral VI this is said to have given rise to the trade name Vicodin.

In the liver, hydrocodone is transformed into several metabolites. It has a serum half-life that averages 3.8 hours. The hepatic cytochrome P450 enzyme CYP2D6 converts it into hydromorphone, a more potent opioid. However, extensive and poor cytochrome 450 CYP2D6 metabolizers had similar physiological and subjective responses to hydrocodone, and CYP2D6 inhibitor quinidine did not change the responses of extensive metabolizers, suggesting that inhibition of CYP2D6 metabolism of hydrocodone has no practical importance. Ultra-rapid CYP2D6 metabolizers (1-2% of the population) may have an increased response to hydrocodone; however, hydrocodone metabolism in this population has not been studied.

A major metabolite, norhydrocodone, is predominantly formed by CYP3A4-catalyzed oxidation. Inhibition of CYP3A4 in a child, who was, in addition, a poor CYP2D6 metabolizer, resulted in a fatal overdose of hydrocodone. Approximately 40% of hydrocodone metabolism is attributed to non-cytochrome-catalyzed reactions.

Taking hydrocodone with grapefruit juice is believed to enhance its narcotic effect. It is hypothesized that the CYP3A4 inhibitors in grapefruit juice may interfere with the metabolism of hydrocodone although there has been no research into this issue. Additionally, many medications are either substrates (competing for metabolism and exhausting available enzymes) or direct inhibitors of CYP3A4. Inhibition of another enzyme, CYP2D6, would also increase the duration of hydrocodone's elevated concentration in the blood, leading to exaggerated effects. Complete inhibition of both enzymes would theoretically inhibit 60% of the factors involved in hydrocodone metabolism, inducing CYP2D6 with, for example, glutethimide or promethazine, also increases the hydrocodone-hydromorphone conversion in the liver, and promethazine is an opioid potentiator used with everything from codeine to alphaprodine in clinical settings, which may increase effects but also muddy the picture vis à vis serum levels at any given time.

Hydrocodone concentrations are measured in blood, plasma, and urine to seek evidence of misuse, to confirm diagnoses of poisoning, and to assist in investigations into deaths. Many commercial opiate screening tests react indiscriminately with hydrocodone, other opiates, and their metabolites, but chromatographic techniques can easily distinguish hydrocodone uniquely. Blood and plasma hydrocodone concentrations typically fall in the 5-30 μg/L range among people taking the drug therapeutically, 100-200 μg/L among recreational users, and 100-1,600 μg/L in cases of acute, fatal overdose.

Many users of hydrocodone report a sense of satisfaction (euphoria), especially at higher doses. A number of users also report a warm or pleasant numbing sensation throughout the body, one of the best-known effects of narcotics. A simultaneous warming of the stomach and rest of the body with the possible sensation of pleasant cooling in the lungs is sometimes also reported, as with opium and hydromorphone.

Currently marketed formulations containing hydrocodone include ZOHYDRO ER™ (extended release pure hydrocodone product, in doses of 10 mg, 15 mg, 20 mg, 30 mg, 40 mg, and 50 mg; releases the drug over 12 hours), HYSINGLA® ER (maximum dose 120 mg hydrocodone), VICODIN® (hydrocodone and acetaminophen), NORCO® (hydrocodone and acetaminophen).

The dose of therapeutic agent depends on the therapeutic agent, the patient, and the condition being treated. For instance, with opioid agonist analgesics, the amount of opioid administered to be effective depends on the opioid itself, the patient's current state, the patient's past history with opioid analgesics, and the condition being treated. That said, the dosages of opioid in immediate release and controlled release formulations are well documented.

Examples of effective and maximal recommended doses of various narcotics are shown below in Table 1 for immediate release formulations. Oral dosage forms comprising opioid agonists are found in U.S. Pat. No. 8,518,443 and U.S. 2007/0185145, the entire contents of which are hereby incorporated by reference in their entirety. The following examples are non-limiting and appropriate dosages may be easily determined by the skilled artisan.

TABLE 1

Exemplary Oral Daily Doses of Narcotics for Analgesic Purposes

| Drug | Single Unit Dose (time period) | Daily Maximum Dose |
| --- | --- | --- |
| Codeine | 15-120 mg | 360 mg |
| Hydrocodone | 2.5-10 mg | 60 mg |
| Hydromorphone | 2-8 mg (3-4 hr) | 60 mg |
| Levorphanol | 2-4 mg (6-8 hr) | 30 mg |
| Meperidine | 50-150 mg (2-4 hr) | 1800 mg |
| Methadone | 5-10 mg (4-12 hours, for pain) 15-40 mg (day, for detoxification) 20-120 mg (day, for opiate dependence maintenance treatment) | |
| Oxycodone | 2.5-5 mg (6 hours) (much higher doses in opiate dependent patients) | |

The term "steady state" means that a plasma concentration for a given drug has been achieved and which is maintained with subsequent doses of the drug at a concentration which is at or above the minimum effective therapeutic concentration and is below the minimum toxic plasma concentration for a given drug. For opioid analgesics, the minimum effective therapeutic concentration will be a partially determined by the amount of pain relief achieved in a given patient. It will be well understood by those skilled in the medical art that pain measurement is highly subjective and great individual variations may occur among patients.

In one embodiment, the pharmaceutical composition comprises a daily dose of a benzodiazepine. The daily dose of a benzodiazepine is typically, e.g., at least 0.25 mg, at least 0.5 mg, at least 0.75 mg, at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 or more mg.

The daily dose of a benzodiazepine is typically about 0.25 mg to about 800 mg, more particularly 0.25 mg to 100 mg, and most typically 0.25 mg to 50 mg. The equivalencies of various benzodiazepines are demonstrated in the Ashtone Equivalency Table, and are reported below: alprazolam (1.5 mg); bentazepam (25 mg); bretazenil (0.5 mg); bromazepam (5-6 mg); brotizolam (0.25 mg); camazepam (10 mg); chlordiazepoxide (25 mg); cinolazepam (40 mg); clobazam (20 mg); clonazepam (0.5 mg); clorazepate (15 mg); clotiazepam (5-10 mg); cloxazolam (1 mg); delorazepam (1 mg); deschloroetizolam (about 2 mg); diazepam (10 mg); diclazepam (1-1.5 mg); estazolam (2 mg); ethyl carfluzepate (2 mg); etizolam (1 mg); ethyl loflazepate (2 mg); flubromazepam (4-6 mg); flunitrazepam (1 mg); flurazepam (15-30 mg); flutoprazepam (2-3 mg); halazepam (20-40 mg); ketazolam (15-30 mg); loprazolam (2 mg); lorazepam (1 mg); lormetazepam (1.5 mg); medazepam (10 mg); midazolam (7.5 mg); nimetazepam (5 mg); nitrazepam (10 mg); nordiazepam (15 mg); oxazepam (25 mg); phenazepam (1 mg); pinazepam (20 mg); prazepam (15 mg); premazepam (15 mg); pyrazolam (1 mg); quazepam (20 mg); temazepam (10 mg); tetrazepam (100 mg); and triazolam (0.25 mg). The recommended dosage for diazepam (VALIUM®) is 2-10 mg every 612 hours, and no more than 30 mg every 8 hours. Based on the equivalency measures, the equivalent dose of Alprazolam (XANAX®) would be 0.5 mg.

In one embodiment, the pharmaceutical composition comprises a daily dose of an antihistamine. A daily oral dose of any given antihistamine may be easily determined by the skilled artisan, but ranges typically from 0.25 mg to 500 mg. In aspects of this embodiment, the daily dose of an antihistamine is typically, e.g., at least 0.25 mg, at least 0.5 mg, at least 0.75 mg, at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 or more mg, at least 100 or more mg, at least 100 or more mg, at least 100 or more mg, at least 100 or more mg, at least 125 or more mg, at least 150 or more mg, at least 175 or more mg, at least 200 or more mg, at least 225 or more mg, at least 250 or more mg, at least 275 or more mg, at least 300 or more mg, at least 325 or more mg, at least 350 or more mg, at least 375 or more mg, at least 400 or more mg, at least 425 or more mg, at least 450 or more mg, at least 475 or more mg, or at least 500 or more mg.

In one embodiment, the pharmaceutical composition comprises a daily dose of a barbiturate. A daily oral dose of any given barbiturate may be easily determined by the skilled artisan, but ranges typically from 0.25 mg to 50 mg. In aspects of this embodiment, the daily dose of an antihistamine is typically, e.g., at least 0.25 mg, at least 0.5 mg, at least 0.75 mg, at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 or more mg, at least 100 or more mg, at least 100 or more mg, at least 100 or more mg, at least 100 or more mg, at least 125 or more mg, at least 150 or more mg, at least 175 or more mg, at least 200 or more mg, at least 225 or more mg, at least 250 or more mg, at least 275 or more mg, at least 300 or more mg, at least 325 or more mg, at least 350 or more mg, at least 375 or more mg, at least 400 or more mg, at least 425 or more mg, at least 450 or more mg, at least 475 or more mg, or at least 500 or more mg.

In one embodiment, the pharmaceutical composition comprises a daily dose of a NSAID. A daily oral dose of any given NSAID may be easily determined by the skilled artisan, but ranges typically from 0.25 mg to 500 mg. In aspects of this embodiment, the daily dose of an antihistamine is typically, e.g., at least 0.25 mg, at least 0.5 mg, at least 0.75 mg, at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 or more mg, at least 100 or more mg, at least 100 or more mg, at least 100 or more mg, at least 100 or more mg, at least 125 or more mg, at least 150 or more mg, at least 175 or more mg, at least 200 or more mg, at least 225 or more mg, at least 250 or more mg, at least 275 or more mg, at least 300 or more mg, at least 325 or more mg, at least 350 or more mg, at least 375 or more mg, at least 400 or more mg, at least 425 or more mg, at least 450 or more mg, at least 475 or more mg, or at least 500 or more mg.

In one embodiment, the pharmaceutical composition comprises a daily dose of an opioid or opioid receptor agonist, e.g., a mu or kappa receptor agonist. A daily oral dose of any given opioid receptor agonist may be easily determined by the skilled artisan, but ranges typically from 0.25 mg to 50 mg. In aspects of this embodiment, the daily dose of an antihistamine is typically, e.g., at least 0.25 mg, at least 0.5 mg, at least 0.75 mg, at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 or more mg, at least 100 or more mg, at least 100 or more mg, at least 100 or more mg, at least 100 or more mg, at least 125 or more mg, at least 150 or more mg, at least 175 or more mg, at least 200 or more mg, at least 225 or more mg, at least 250 or more mg, at least 275 or more mg, at least 300 or more mg, at least 325 or more mg, at least 350 or more mg, at least 375 or more mg, at least 400 or more mg, at least 425 or more mg, at least 450 or more mg, at least 475 or more mg, or at least 500 or more mg.

The present compositions include a respiratory stimulant. In one embodiment, the respiratory stimulant directly stimulates chemoreceptors in the carotid bodies of the carotid arteries which then act centrally on the brainstem to stimulate respiration. In a further embodiment, the respiratory stimulant does not antagonize the opioid mu receptor.

In one embodiment the respiratory stimulant is doxapram (marketed as DOPRAM™, STIMULEX™, or RESPIRAM™ for human use and DOPRAM™ for veterinary use), modafinil, almitrine, AMPAkines, GAL-021, buspirone, mosapride, CX546, CX717, pharmaceutically acceptable salts thereof, and combinations thereof. In one aspect, the respiratory stimulant is doxapram, modafinil, or almitrine, pharmaceutically acceptable salts thereof, and combinations thereof.

In one embodiment, the doxapram is DOPRAM™, i.e., doxapram hydrochloride having the chemical name of 1-ethyl-4-[2-(4-morpholinyl)ethyl]-3,3-diphenyl-2-pyrrolidinone monohydrochloride, monohydrate.

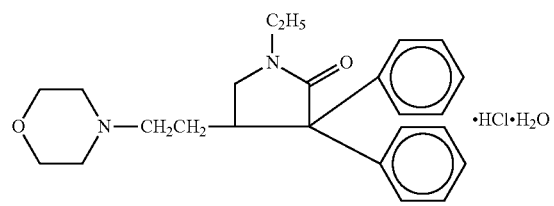

Doxapram is approved by the FDA for (1) stimulation of respiration in the postoperative patient, and in patients with drug-induced post-anesthesia respiratory depression or apnea, (2) to stimulate respiration, hasten arousal and return airway protective reflexes in patients with respiratory and CNS depression due to drug overdose, and (3) to stimulate respiration in chronic pulmonary disease patients with acute respiratory insufficiency. For intravenous doxapram, the onset is 20-40 seconds and the duration of effect is 5-12 minutes, the peak plasma time is 1-2 minutes and the half-life is 3.4 hours. Intravenous DOPRAM™ is administered with 20 mg doxapram hydrochloride in water. However, doxapram increases tidal volume and potentially also respiratory rate. Side effects include hypertension, anxiogenesis, and dyspnea.

The primary limitation to more widespread use of doxapram is its analeptic effect. Previously, this property was desirable and used to hasten recovery from anesthesia. With use of shorter-acting anesthetic agents, the need for stimulants has diminished and the analeptic properties of doxapram are more evident. In combination with opioids at higher doses, this analeptic effect may be tempered.

Doxapram is used in intensive care settings to stimulate the respiratory rate in patients with respiratory failure. It may be useful for treating respiratory depression in patients who have taken excessive doses of drugs such as buprenorphine, which may fail to respond adequately to treatment with naloxone. It has also been used in combination with morphine in a postoperative setting as an intravenous administration. See e.g., Gupta et al., Anaesthesia, 1974, Vol. 29, pages 33-39, the entire contents of which are incorporated by reference.

It is equally effective as pethidine in suppressing shivering after surgery. See Clyburn, Anaesthesia, 1988, Vol. 43, pages 190-193, the entire contents of which are hereby incorporated by reference. Side effects include high blood panic attacks, rapid heart rate, tremor, sweating and pressure, vomiting. Convulsions have been reported. Its use is relatively contraindicated in people with coronary heart disease, epilepsy, and high blood pressure. It is also contraindicated in newborns and small children, mainly due to the presence of benzyl alcohol, which is included as a preservative.

Doxapram is panicogenic and patients with a panic disorder exhibit increased sensitivity to doxapram. Panic disorders and abrupt increases in arousal can elicit hyperventilation. This relationship may explain why residual ventilatory stimulation persists following doxapram administration in carotid denervated/ablated animals and humans.

The pressor effects of doxapram have been recognized since its initial use. In humans and dogs, the pressor effect in normotensive individuals has been described as "slight" with a larger sustained increase in blood pressure and cardiac output documented in hypotensive individuals. The mechanism whereby doxapram increases blood pressure is unknown but may be related to increase in circulating catecholamine levels during administration.

Doxapram increases heart rate in multiple species. The effects on cardiac rhythm are less consistent. Doxapram prolongs the QT interval on electrocardiograms in premature infants by an unknown mechanism. Drug-induced prolongation of the QT interval may be followed by potentially fatal arrhythmias, such as Torsade de pointes. In terms of severe life-threatening side effects, doxapram is described as having a wide therapeutic window (in humans ~20-40 fold). At toxic single doses in animals (e.g., rat LD50=72 mg/kg IV), the primary manifestation of toxicity is CNS excitation including hyperactivity, tremors, tonic-clonic movements, and convulsions. Other symptoms include salivation, diarrhea, emesis, urination, and defecation. Doxapram is proconvulsant but only at doses much higher than those that evoke respiratory stimulation.

Doxapram is racemic, and exists as a racemate with dextrorotatory (+) and levorotatory (−) enantiomers. There is considerable precedent in the literature for the pharmacokinetic and pharmacodynamic properties of chiral drugs to be stereoselective. In these instances the enantiomer possessing the desirable pharmacological properties is termed the eutomer, whereas the enantiomer lacking such properties is termed the distomer. The respiratory stimulant properties of doxapram could be stereoselective and could be evaluated by chirally separating doxapram into its (+) enantiomer (GAL-054) and (−) enantiomer (GAL-053). Preclinically we demonstrated that the (+) enantiomer, GAL-054, and not the (−) enantiomer, GAL053, dose-dependently increased minute volume when administered intravenously to drug naïve and opioid challenged rats and cynomolgus monkeys. Moreover, the deleterious side effects of agitation and seizures were restricted to GAL-053. There were minimal behavioral changes observed in rats and monkeys receiving GAL-054. Thus, GAL-054 is the eutomer and GAL-053 the distomer of doxapram. Unfortunately, in conscious rats GAL-054 increased blood pressure approximately 15-20% above baseline values at doses that were moderately respiratory stimulant. This effect was confirmed in a Phase 1 clinical trial evaluating the effects of GAL-054 in healthy volunteers. Thus, the ventilatory stimulant and pressor effects of doxapram cannot be separated by enantiomeric separation of the racemate.

Thus, in one embodiment, the peak plasma concentration of doxapram ranges from about 1 µg/ml to 50 µg/ml, about 5 µg/ml to about 45 µg/ml, about 5 µg/ml to about 40 µg/ml, about 5 µg/ml to about 35 µg/ml, about 5 µg/ml to about 30 µg/ml, about 5 µg/ml to about 25 µg/ml, about 1 µg/ml to about 45 µg/ml, about 1 µg/ml to about 40 µg/ml, about 1 µg/ml to about 35 µg/ml, about 1 µg/ml to about 30 µg/ml, about 1 µg/ml to about 25 µg/ml, about 1 µg/ml to about 20 µg/ml, about 1 µg/ml to about 15 µg/ml, about 1 µg/ml to about 10 µg/ml, about 1 µg/ml to about 9 µg/ml, about 1 µg/ml to about 8 µg/ml, about 1 µg/ml to about 7 µg/ml, about 1 µg/ml to about 6 µg/ml, and about 1 µg/ml to about 5 µg/ml.

In a further embodiment, the peak plasma concentration of doxapram is at least 0.25 µg/ml, at least 0.5 µg/ml, at least 0.75 µg/ml, at least 1 µg/ml, at least 2 µg/ml, at least 3 µg/ml, at least 4 µg/ml, at least 5 µg/ml, at least 6 µg/ml, at least 7 µg/ml, at least 8 µg/ml, at least 9 µg/ml, at least 10 µg/ml, at least 15 µg/ml, at least 20 µg/ml, at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 80 µg/ml, at least 85 µg/ml, at least 90 µg/ml, at least 95 µg/ml, at least 100 µg/ml or more µg/ml.

A total dose of doxapram administered intravenously ranges from about 1 mg to 10,000 mg, about 10 mg to about 9,000 mg, about 100 mg to about 8,000 mg. A total daily dose of doxapram administered orally ranges from about 0.25 mg/kg to about 150 mg/kg, about 5 mg/kg to about 150 mg/kg, about 10 mg/kg to about 150 mg/kg, about 15 mg/kg to about 150 mg/kg, about 20 mg/kg to about 150 mg/kg, about 25 mg/kg to about 150 mg/kg, about 30 mg/kg to about 150 mg/kg, about 35 mg/kg to about 150 mg/kg, about 5 mg/kg to about 100 mg/kg, about 5 mg/kg to about 90 mg/kg, about 5 mg/kg to about 80 mg/kg, about 5 mg/kg to about 70 mg/kg, about 5 mg/kg to about 60 mg/kg, about 5 mg/kg to about 50 mg/kg, or about 5 mg/kg to about 40 mg/kg. In one embodiment, the dosage form contains at least 50 mg doxapram, at least about 75 mg doxapram, at least about 100 mg doxapram, at least about 125 mg doxapram, at least about 150 mg doxapram, at least about 175 mg doxapram, at least about 200 mg doxapram, at least about 250 mg doxapram, or at least about 300 mg doxapram.

Almitrine bismesylate was developed in the 1970s as a respiratory stimulant and first commercialized in 1984 when it was marketed under the product name VECTARION™, also being sold under the names of ALMITRINE™ (OS: DCF, BAN), S 2620 (IS), ALMITRINE MESYLATE™ (OS: USAN), DUXIL™ (almitrine and raubasine), TRUXIL™ (almitrine and raubasine), ALBASINE™ (almitrine and raubasine), ARMANOR™, (almitrine and raubasine), and PREMODAL™ (almitrine and raubasine). The chemical names for almitrine are N,N'-Diallyl-6-[4-(4, 4'difluorobenzhydryl)piperazin-1-yl]-1,3,5-triazine-2,4-diyldiamine (BAN) and 2,4-Bis(allylamino)6-[4-[bis(p-fluorophenyl)methyl]-1-piperazinyl-s-triazine (WHO).

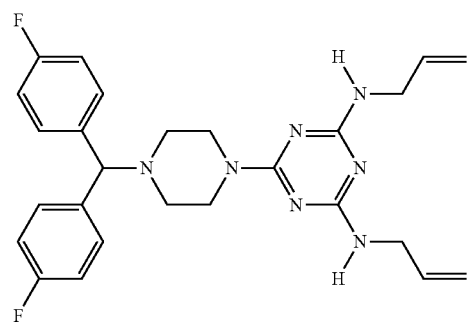 [SMILES: C=CCNc1nc(NCC=C)nc(N2CCN(C(c3ccc(F)cc3)c3ccc(F)cc3)CC2)n1]

In the past, almitrine was used intravenously in the perioperative setting for indications mirroring those for doxapram, except not as an analeptic agent. Nowadays, albeit with declining frequency, almitrine is used chronically in the management of chronic obstructive pulmonary disease (COPD).

Almitrine has never been licensed for use in the United States. In the European Union, availability is limited to France, Poland and Portugal, where its primary indication is to improve oxygenation in patients with chronic obstructive pulmonary disease. The European Medicines Agency has started a review of almitrine related to adverse side effects including weight loss and peripheral neuropathies.

Almitrine increases VE by increasing VT and/or RR across multiple species. Almitrine is also efficacious in the face of an opioid challenge. As discussed above, the effects of almitrine on breathing are solely due to stimulation of the peripheral chemoreceptors. The effects of almitrine on ionic currents from isolated rat type 1 glomus cells have been reported. Almitrine inhibits BK currents (1050-200 nM) without altering voltage dependent K+, Na+, or calcium currents. To our knowledge, the effect of almitrine on TASK channels has not been tested.

Only one of almitrine's metabolites is active, but its potency as a respiratory stimulant is 5 times less than the parent compound. Almitrine improves post-operative indices of ventilation while causing a mild decrease in blood pressure and no change in heart rate or cardiac output. Contrasting with the pressor effects of doxapram. Almitrine's primary use is as a respiratory stimulant in people with COPD. Almitrine increases ventilation in patients with COPD, significantly improving blood gases and reducing the incidence of intubation when compared to placebo controls.

At doses that do not increase VE, almitrine is still capable of altering breathing control. This is best illustrated by a study where the effects of gradually increasing the dose of almitrine on hypoxic and hypercapnic sensitivity were evaluated in healthy volunteers. Almitrine dosedependently increased the slopes of the hypoxic (at >50 µg/ml) and hypercapnic (at >200 µg/ml) ventilatory responses without increasing VE on room air. The authors also noted that the effects of almitrine on chemosensitivity persisted despite plasma levels of the drug declining below these thresholds. Small increases in VE (about 11% above baseline) on room air were only observed when plasma concentrations of almitrine exceeded approximately 250 µg/ml. The ability of a carotid body stimulant to increase chemosensitivity without an accompanying increase in VE during normoxia may reflect the limited role of the carotid body in modulating VE during normoxic conditions. Thus, potentiation of carotid body signaling in this scenario may only be evident when an individual is exposed to hypoxia and/or hypercapnia. The persistent effect of almitrine on chemosensitivity despite waning plasma levels may be due to the presence of an active metabolite or tissue binding of the drug within the peripheral chemoreceptors.

Thus, in one embodiment, the effective plasma concentration of almitrine ranges from about 25 µg/ml to 500 µg/ml, about 25 µg/ml to about 450 µg/ml, about 25 µg/ml to about 400 µg/ml, about 25 µg/ml to about 350 µg/ml, about 25 µg/ml to about 300 µg/ml, about 25 µg/ml to about 250 µg/ml, about 50 µg/ml to about 500 µg/ml, about 55 µg/ml to about 500 µg/ml, about 60 µg/ml to about 500 µg/ml, about 65 µg/ml to about 500 µg/ml, about 70 µg/ml to about 500 µg/ml, about 75 µg/ml to about 500 µg/ml, about 80 µg/ml to about 500 µg/ml, about 85 µg/ml to about 500 µg/ml, about 90 µg/ml to about 500 µg/ml, about 95 µg/ml to about 500 µg/ml, about 100 µg/ml to about 500 µg/ml, about 110 µg/ml to about 500 µg/ml, about 120 µg/ml to about 500 µg/ml, about 130 µg/ml to about 500 µg/ml, about 140 µg/ml to about 500 µg/ml about 150 µg/ml to about 500 µg/ml, about 160 µg/ml to about 500 µg/ml, about 170 µg/ml to about 500 µg/ml, about 180 µg/ml to about 500 µg/ml, about 200 µg/ml to about 500 µg/ml, about 200 µg/ml to about 490 µg/ml, about 200 µg/ml to about 480 µg/ml, about 200 µg/ml to about 470 µg/ml, about 200 µg/ml to about 460 µg/ml, about 200 µg/ml to about 450 µg/ml, about 200 µg/ml to about 440 µg/ml, about 200 µg/ml to about 430 µg/ml, about 200 µg/ml to about 420 µg/ml, about 200 µg/ml to about 410 µg/ml, or about 200 µg/ml to about 400 µg/ml.

In a further embodiment, the effective plasma concentration of almitrine is at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 80 µg/ml, at least 85 µg/ml, at least 90 µg/ml, at least 95 µg/ml, at least 100 µg/ml, 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, at least 400 µg/ml, at least 425 µg/ml, at least 450 µg/ml, at least 475 µg/ml, at least 500 µg/ml or more µg/ml.

A total dose of almitrine administered intravenously ranges from about 0.045 µg/kg to 300 µg/kg. A total daily dose of almitrine administered orally ranges from about 0.25 mg/kg to about 15 mg/kg, about 0.25 mg/kg to about 10 mg/kg, about 0.25 mg/kg to about 7.5 mg/kg, about 0.25 mg/kg to about 5 mg/kg, about 0.25 mg/kg to about 2.5 mg/kg, about 0.25 mg/kg to about 2.25 mg/kg, about 0.25 mg/kg to about 2.0 mg/kg, about 0.25 mg/kg to about 1.75 mg/kg, about 0.25 mg/kg to about 1.5 mg/kg, about 0.25 mg/kg to about 1.25 mg/kg, about 0.25 mg/kg to about 0.75 mg/kg, or about 0.25 mg/kg to about 0.5 mg/kg. In one embodiment, the dosage form contains at least 50 mg almitrine, at least about 75 mg almitrine, at least about 100 mg almitrine, at least about 125 mg almitrine, at least about 150 mg almitrine, at least about 175 mg almitrine, or at least about 200 mg almitrine.

Almitrine exerts beneficial effects on pulmonary gas exchange (increased PaO2, and improved ventilation—perfusion ratios—VA/VQ matching) without increasing VE. The mechanism responsible for this effect is believed to be enhanced hypoxic pulmonary vasoconstriction (HPV). Almitrine improves VA/VQ matching in patients with COPD and increases pulmonary vascular resistance consistent with an effect on pulmonary vascular tone. HPV is often depressed peri-operatively, so any new drug for this setting that normalizes HPV would be highly desirable.

Almitrine has a lower therapeutic dose and greater toxic dose than doxapram (almitrine LD50>200 mg/kg in mice cf. doxapram LD50 of 85 mg/kg in mice). Acutely, almitrine is generally well tolerated and safe in humans. Not surprisingly, increased awareness of breathing and breathlessness are the most common side effects following almitrine administration. Other side effects included headache, fatigue, insomnia, malaise, flushing, sweating, and postural dizziness. Gastro-intestinal side effects included nausea, abdominal discomfort, and diarrhea. There are minimal changes in cardiovascular parameters except for a mild increase in pulmonary artery pressure. Almitrine is less tolerated when administered chronically. Multi-year trials observed that patients receiving almitrine exhibited significant weight loss (>15%) that appeared to be anorectic in nature. The most significant and consistent side effect of chronic (more than 3 months) almitrine administration is peripheral neuropathy. Further examination revealed that these patients showed axonal degradation and a decrease in the density of large myelinated fibers. Mechanistic studies in animals identified the detriazinyl metabolite, 4,4'fluorobenzhydrylpiperazine, the major almitrine metabolite formed in humans, as the probable cause of the evoked neuropathy. Thus, the use of almitrine is no longer recommended and is withdrawn or in regulatory review in many countries.

There have been only a few new therapeutic agents developed that focus on respiratory control and even fewer have been approved for clinical use during the previous decades. One issue has been poor translation of pre-clinical efficacy into humans, as has occurred with the 5HT1A and 5-HT4 receptors agonists, buspirone and mosapride. However, salts of such drugs and particular formulations are of interest in the present compositions. AMPAkines and GAL-021.

AMPAkines are modulators of α-amino-3-hydroxy-5-methyl-4-isoxazolepropionic acid (AMPA) receptors and have been widely explored for a variety of neuropsychiatric diseases including schizophrenia and epilepsy. Cognitive improvement has been the primary focus of most research with this drug class. Glutamate acting via AMPA receptors is essential for maintaining respiratory rhythmogenesis at the purported kernel of rhythm generation, the preBotzinger complex in the hindbrain. Thus, the rationale for the use of AMPAkines to treat respiratory depression, in particular the type caused primarily by a decrease in respiratory rate or opioid-induced respiratory depression is that positive allosteric modulators of AMPA receptors would enhance respiratory rhythm. Various AMPAkines (Cortex Pharmaceuticals, Inc.) have been evaluated preclinically and clinically as respiratory stimulants. The positive AMPA allosteric modulator CX546 reversed the ventilatory suppressive effects of fentanyl and phenobarbital in the rat. A second AMPA receptor modulator, CX717, has been tested preclinically and is also able to reverse the respiratory depressive effects of fentanyl, alcohol and pentobarbital. CX717 also reverses opiate suppression of hypoglossal motor neurons. In young healthy subjects with a target alfentanil infusion concentration of 100 μg/ml (i.e., analgesic), CX717 at a dose of 1,500 mg prevented the fall in respiratory rate vs. placebo. See Oertel B G, Felden L, Tran P V, Bradshaw M H, Angst M S, Schmidt H, Johnson S, Greer J J, Geisslinger G, Varney M A, Lötsch J (February 2010). "Selective antagonism of opioid-induced ventilatory depression by an ampakine molecule in humans without loss of opioid analgesia". Clinical Pharmacology and Therapeutics 87 (2): 204-11. However, in that study there also was an interaction between alfentanil and CX717 with respect to visual analog scale parameter "tiredness", in that the participants receiving CX717 reported increased tiredness compared to placebo controls.

In humans, AMPAkines improved memory and information processing in the healthy elderly and people with schizophrenia. In a randomized, double blind, crossover study in sleep deprived young subjects, CX717 enhanced cognitive performance and alertness. Slow wave sleep was reduced and recovery sleep impaired. Thus, the respiratory stimulatory effects of new AMPAkine molecules are associated with stimulatory neuropsychiatric effects on arousal-alertness state and cognitive performance. Additional AMPAkines of potential interest include CX 516, CX614, and CX1739, which are structurally related and may have increased bioavailability. Structures of three AMPAkines are provided below:

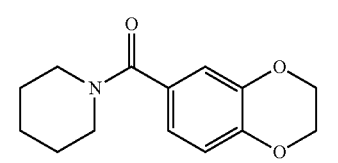

1-(1,4-benzodioxan-6-ylcarbonyl)piperidine
CX546

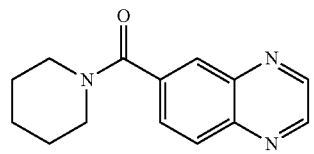

1-(quinoxalin-6-ylcarbonyl)piperidine
CX516

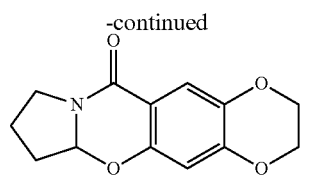

2H,3H,6aH-pyrrolidino[2″,1″-3′,2′]1,3-oxazino[6′,5′-5,4]benzo[e]1,4-dioxan-10-one
CX614

The daily dose of AMPAkines may differ from drug to drug, but a range of about 100-5,000 mg has been reported to be effective in humans. In one embodiment, the dose of AMPAkine ranges from about 200 mg to about 1,800 mg. In a further aspect, the daily dose of AMPAkine ranges from about 250 mg to about 1,500 mg. In yet a further aspect, the daily dose of AMPAkine ranges from about 250 mg to about 2,000 mg, about 250 mg to about 1,750 mg, about 250 mg to about 1,500 mg, about 300 mg to about 1,200 mg, about 500 mg to about 1,000 mg, about 600 mg to about 800 mg. In still a further aspect, with the more bioavailable/bioactive AMPAkines, the daily dose ranges from about 100 mg to about 1,000 mg, about 150 mg to about 1,000 mg, about 200 mg to about 1,000 mg, about 250 mg to about 1,000 mg, about 300 mg to about 1,000 mg, about 350 mg to about 1,000 mg, about 400 mg to about 1,000 mg, about 450 mg to about 1,000 mg, about 500 mg to about 1,000 mg, about 100 mg to about 500 mg, about 150 mg to about 500 mg, about 200 mg to about 500 mg, or about 250 mg to about 500 mg.

The daily dose of AMPAkines may differ from drug to drug, but is typically, e.g., at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, at least 1000 mg, at least 1050 mg, at least 1100 mg, at least 1150 mg, at least 1200 mg, at least 1250 mg, at least 1300 mg, at least 1350 mg, at least 1400 mg, at least 1450 mg, at least 1500 mg or more mg.

Agents that increase the drive to breathe by mimicking the effects of acute hypoxia and/or hypercapnia at the level of the peripheral chemoreceptors represent a rational approach toward the development of therapeutics for breathing control disorders that would benefit from ventilatory stimulation. GAL-021 (Galleon Pharmaceuticals, Inc.), a BK channel blocker, is currently in early clinical trials. GAL-021 is a calcium-activated potassium (BKe) channel blocker that causes reversal of opioid-induced respiratory depression in animals due to a stimulatory effect on ventilation at the carotid bodies. In 2014, a study was made to assess in humans whether GAL-021 stimulates breathing in established opioid-induced respiratory depression and to evaluate its safety (see McLeod and Dahan, Anesthesiology, v. 121, n. 3, page 3A, September 2014, the entire contents of which are herein incorporated by reference). The study involved two parts. The first study involved a proof-of-concept double-blind randomized controlled crossover study on iso-hypercapnic ventilation (study 1) and the second, was a double blind exploratory study on poikilocapnic ventilation and nonrespiratory end points (study 2). In study 1, intravenous low- and high-dose GAL-021 and placebo were administrated on top of low- and high-dose alfentanil-induced respiratory depression in 12 healthy male volunteers on two separate occasions. In study 2, the effect of GAL-021 placebo on poikilocapnic ventilation, analgesia, and sedation were explored in eight male volunteers. The results of Study 1 suggested that under isohypercapnic conditions, a separation between GAL021 and placebo on minute ventilation was observed by 6.1 (3.6 to 8.6) 1/min (P<0.01) and 3.6 (1.5 to 5.7) 1/min (P<0.01) at low-dose alfentanil plus high-dose GAL-021 and high-dose alfentanil plus high-dose GAL-021, respectively. The results of Study 2 noted similar observations on poikilocapnic ventilation and arterial pCO2, GAL-021 had no effect on alfentanil-induced sedation, antinociception and no safety issues or apparent hemodynamic effects. The conclusion of the study suggested that GAL-021 produced respiratory stimulatory effects during opioid-induced respiratory depression with containment of opioid-analgesia and without any further increase in sedation.

GAL-021 is a new chemical entity designed based on understanding of the structure—activity relationship and structure-tolerability limitations of almitrine. GAL-021 does not contain the fluorinated piperazine ring, which causes lipidosis in dorsal root ganglia in rat leading to peripheral neuropathy and hind limb dysfunction. GAL-021 was extensively profiled in mice, rats, dogs, and cynomolgus monkeys preclinically. In brief, GAL-021 stimulates ventilation and attenuates opiate-induced respiratory depression but not morphine analgesia. GAL-021 also reverses drug-induced respiratory depression elicited by Isoflurane, Propofol, and Midazolam (Galleon Pharmaceuticals, unpublished data). Ventilatory stimulation is accompanied by enhanced carotid sinus nerve afferent and phrenic nerve efferent activity. Carotid sinus nerve transection almost completely abolishes (about 85% reduction) GAL-021-induced respiratory stimulation. The residual stimulation was blocked when the cervical vagi were transected in addition to the carotid sinus nerve (Galleon Pharmaceuticals, unpublished data). Thus, some of the effects of GAL-021 on ventilation are mediated from other peripheral sites, most likely aortic chemoreceptors.

In healthy human subjects, GAL-021 administration caused statistically significant increases in VE (AUE 0-1 h) with reciprocal suppression of ETCO2 during 1-h continuous infusions. The half-maximal effect on VE and ETCO2 occurred rapidly (<10 min). Drug concentration rose rapidly during the infusion and declined rapidly initially with a distribution t1/2 of 30 min and then more slowly with a terminal t1/2 of 5-7 h. Thus, in humans GAL-021 has pharmacodynamic and pharmacokinetic characteristics consistent with an acute care medication. A Proof-of-Concept study using opioids in a hypercapnic clamp setting is ongoing in humans to determine the clinical utility of GAL-021 and to validate the BK channel as a therapeutic target. Further clinical development with phase 2 studies in patients with postoperative respiratory depression show follow.

In one embodiment, the respiratory stimulant, or drug of interest is modafinil.

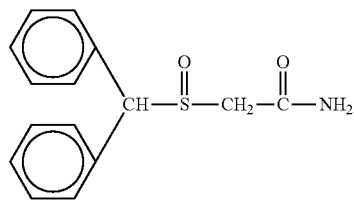

In the literature, it was found that a single dose of modafinil might hasten recovery from general anesthesia after day surgery. Additionally, a single dose of modafinil improved the ability of emergency room physicians to attend didactic lectures after a night shift, but did not improve their ability to drive home and caused sleep disturbances subsequently. Modafinil had a substantial placebo effect on outcomes such as fatigue, excessive sleepiness and depression in patients with traumatic brain injury, major depressive disorder, schizophrenia, post-polio fatigue and multiple sclerosis. However, it did not provide any benefit greater than placebo. Trials of modafinil for excessive sleepiness in Parkinson's disease, cocaine addiction and cognition in chronic fatigue syndrome provided inconsistent results.

In one embodiment, an effective daily dose of modafinil as used herein may range from about 25 mg to about 500 mg, about 50 mg to about 500 mg, about 100 mg to about 500 mg, about 150 mg to about 500 mg, about 200 mg to about 500 mg, about 50 mg to about 250 mg, about 75 mg to about 250 mg about 100 mg to about 250 mg, about 125 mg to about 250 mg, about 150 mg to about 250 mg, about 175 mg to about 250 mg, about 200 mg to about 250 mg, about 25 mg to about 225 mg, about 25 mg to about 200 mg, about 25 mg to about 175 mg, about 25 mg to about 150 mg, or about 50 mg to about 150 mg. In one embodiment, the dose of modafinil in the present compositions is at least 50 mg, at least 75 mg, at least 100 mg, at least 125 mg, at least 150 mg, at least 175 mg, at least 200 mg, at Modafinil is a wake-n promoting agent that is pharmacologically different from other stimulants. The exact mechanism of action of modafinil is unclear. Its neurochemical effects have been reviewed recently. In animal studies, modafinil has been shown to interact with dopaminergic, noradrenergic, glutamatergic, GABAergic, serotoninergic, orexinergic, and histaminergic pathways. It has been investigated in healthy volunteers, and in individuals with clinical disorders associated with excessive sleepiness, fatigue, impaired cognition and other symptoms. In sleep-deprived individuals, modafinil improves mood, fatigue, sleepiness and cognition to a similar extent as caffeine but has a longer duration of action. Evidence for improved cognition in non-sleep-deprived healthy volunteers is controversial. Modafinil improves excessive sleepiness and illness severity in all three disorders for which it has been approved by the US FDA, i.e. narcolepsy, shift work sleep disorder and obstructive sleep apnea with residual excessive sleepiness despite optimal use of continuous positive airway pressure (CPAP).

Modafinil induces and inhibits several cytochrome P450 isoenzymes and has the potential for interacting with drugs from all classes. The modafinil dose should be reduced in the elderly and in patients with hepatic disease. Caution is needed in patients with severe renal insufficiency because of substantial increases in levels of modafinil acid. Common adverse events with modafinil include insomnia, headache, nausea, nervousness and hypertension. Decreased appetite, weight loss and serious dermatological have been reported with greater frequency in children and adolescents, probably due to the higher doses (based on bodyweight) used. Modafinil may have some abuse/addictive potential although no cases have been reported to date.

The exact mechanism of action of modafinil is unclear. Its neurochemical effects have been reviewed recently. In animal studies, modafinil has been shown to interact with dopaminergic, noradrenergic, glutamatergic, GABAergic, serotoninergic, orexinergic, and histaminergic pathways.

Effects of Modafinil on the Dopaminergic Pathways: The evidence regarding modafinil and dopaminergic pathway interactions is contradictory. Initial studies showed modafinil had only a weak affinity for dopamine receptors, it did not stimulate release of dopamine in the mouse caudate nucleus. or mouse synaptosome preparations preloaded with 3H1dopamine, and it did not affect the firing rate of the dopaminergic neurons in the rat midbrain. Various dopamine D1 and D2 receptor antagonists did not suppress the modafinilinduced hyperactivity in mice, the modafinil-induced arousal in cats or the modafinil-induced reduction in stop signal reaction time in rats. Furthermore, inhibition of dopamine synthesis did not decrease the hyperactivity associated with modafinil in mice and only slightly reduced the arousal effects of modafinil in cats. However, more recent studies show that modafinil administration in different doses and routes leads to increased extracellular levels of dopamine in the rat prefrontal cortex, the narcoleptic dog caudate nucleus, rat nucleus accumbens and rat striatal slices preloaded with [3H]dopaminepl] Conversely, modafinil inhibits the dopaminergic neurons in the ventral tegmental area and the substantia nigra; this inhibition is abolished by sulpiride (a D2-recepror antagonist) and by nomifensine (a dopamine reuptake inhibitor). In rhesus monkeys, modafinil occupies the striatal dopamine transporter (DAT) and in vitro inhibits dopamine transport. Furthermore, the wake-promoting effects of modafinil are lost in DAT knockout mice. Thus, contrary to earlier literature, new evidence is emerging that indicates a role for dopaminergic pathways in the actions of modafinil. Some of the earlier studies may have been negative because relatively lower doses of modafinil were used.

Effects of Modafinll on Noradrenergic pathways: The evidence for modafinil action being mediated by noradrenergic pathways is also controversial. Modafinil does not bind to adrenergic receptors at physiological doses, it does not affect the firing rate of the rat pontine noradrenergic neurons and it does little to reduce cataplexy that normally responds to alpha 1-receptor agonists or to agents that block the reuptake of noradrenaline (norepinephrine) by noradrenaline transporter (NAT). On the other hand, modafinil use leads to increased levels of noradrenaline in the rat prefrontal cortex and medial hypothalarnus. In rat brain slices, modafinil increases the inhibitory effects of noradrenaline on VLPO neurons. Various alpha adrenoceptor antagonists attenuate the modafinil-induced arousal in cats and locomotor activity in mice and monkeys. The modafinil response is significantly reduced in genetically alpha1-B-adrenoceptor-deficient mice. Furthermore, modafinil occupies NAT sites in the thalamus of rhesus monkeys in vivo and blocks noradrenaline transport via NAT in vitro. Thus, it appears that noradrenergic pathways are also important for the action of modafinil.

Interactions of modafinil, Dopaminergic and Adrenergic Signaling: The action of modafinil is not blocked in mice treated with N-(2-chloroethyl)-N-ethyl 2-bromobenzylamine, a toxin that destroys all NAT-bearing forebrain noradrenergic projections, suggesting that forebrain NAT is not important in the action of modafinil However, pretreatment with quinpirole (a dopamine autoreceptor agonist which suppresses dopamine release) or terazosin (an alphaadrenocepror antagonist) blocked the action of modafinil in these mice. This suggests that nonnoradrenergic, dopamine-dependent adrenergic stimulation is essential for action of modafinil and implies dopamine may directly stimulate adrenergic receptors.

Several studies have looked at GABA and/or glutamate levels in various areas of the brain in response to modafinil. In general, the two neurotransmitters have an inverse relationship. With modafinil administration, levels of the activating neurotransmitter glutamate are increased in the thalamus, hippocampus, striarum, medial pre-optic area (MPA) and the posterior hypothalamus of the rat brain. The GABA A-receptor agonist muscimol decreased, whereas the GABA A-receptor antagonist bicuculline augmented the levels of glutamate in the posterior hypothalamus and MPA; thus, it appears that the glutamate levels in these areas increase when the inhibitory GABAergic tone decreases and glutamate levels decrease when GABAergic tone increases. GABA levels decrease with modafinil in the guineapig and rat cortex, the rat MPA and posterior hypothalamus, hippocampus, nucleus accumbens, striatum, globus pallidus and substantia nigra. The effects of modafinil on GABA and glutamate levels may be region specific. An intact catecholamine system is important for these changes because pretreatment with dopaminergic neurotoxin and an Alpha-1-adrenoceptor antagonist reversed the modafinil effects on GABA. Serotonin and GABA also seem to have an inverse relationship. In many brain areas, including the frontal cortex, central nucleus of amygdala, DR, MPA and posterior hypothalamus, modafinil decreases levels of GABA, but increases levels of serotonin. Moreover, the effects of modafinil on GABA release are abolished by serotoninergic inhibitors and serotonin selective neurotoxins. Serotonin reuptake inhibitors (SRIs) enhance the effect of modafinil on serotonin levels. Thus, modafinil seems to lower the levels of the inhibitory neurotransmitter GABA, and increase glutamate and serotonin levels in several areas of the brain; intact catecholamine and serotonin systems are essential for effects on GABA.

Modafinil also interacts with orexin neurons in the brain; patients with narcolepsy deficient orexin benefit from modafinil. However, modofinil is more effective in producing wakefulness in orexin knockout mice than in wild-type litter mates. Therefore, the interactions of modafinil with orexin neurons seem complicated and unclear at present.

Effects of Modafinil on Histaminergic Pathways: Modafinil increases Fos immunoreactivity in the histaminergic TMN, and histamine levels in the anterior hypothalamus in rats are increased with intraperitoneal and intracerebroventricular injections of modafinil, although direct injection into the TMN does not produce this effect. The locomotor activity of rats is also increased with intraperitoneal administration of modafinil, which is reversed with depletion of neuronal histamine in mice. Therefore, histamine seems to be important for the locomotion effects of modafinil.

In summary, modafinil actions seem to be related to decreased GABA and increased glutamate levels; intact catecholamine (including dopamine) and serotonin systems are essential for modafinil effects on GABA. Histaminergic and adrenergic systems seem to be important for modafinil effects on loco-motion.

Potential Side Effects of the Respiratory Stimulant: Doxapram and almitrine illustrates the potential utility of a carotid body stimulant in the treatment of drug-induced respiratory depression, and possibly exacerbated sleep disordered breathing in the perioperative setting. However, the widespread use of both drugs may be limited by their side effect profiles and toxicities. In the case of doxapram, the primary limitation is in its pressor effects. There is controversy over whether the pressor effect is an inherent property of a carotid body stimulant. The answer appeared to be no. Although carotid body stimulation elicits a stereotypical systemic response, which includes a range of cardiovascular reflexes, the precise cardiovascular effect depends upon whether ventilation is, or is not, controlled. For example, if ventilation can increase as in a spontaneously breathing patient, carotid body stimulation typically increases heart rate and decreases systemic vascular resistance with minimal changes or a slight decrease in blood pressure. On the other hand, if ventilation is controlled as in a patient on a ventilator, carotid body stimulation usually causes bradycardia, an increase in vascular resistance, and an associated pressor effect. This dependence on whether breathing is spontaneous or controlled may be related to the interplay of pulmonary vagal afferent feedback and PaCO2 on cardiovascular regulation. It was found that doxapram increased blood pressure in carotid body of denervated rats (Galleon Pharmaceuticals, unpublished data) suggesting that the pressor effects of this compound are due, at least in part, to mechanisms outside of the carotid bodies. Thus, a selective carotid body stimulant with minimal central effects is likely to be better tolerated in the post-operative setting than doxapram. This is evident in the case of almitrine. Almitrine has a myriad of effects that would be beneficial postoperatively, including reversal of drug-induced hypoventilation, enhanced chemosensitivity, decreased plant gain, and improved VA/VQ matching, but with minimal pressor effects. The primary limitation with almitrine is the peripheral neuropathy following chronic use. GAL-021 does not contain the fluorinated piperazine ring associated with this toxicity and appears to retain many of the desirable properties of almitrine.

In one embodiment, the ratio of the total amount of therapeutic agent to the total amount of respiratory stimulant ranges from 1:100 w/w to 100:1 w/w. In this aspect, the ratio of the amount of therapeutic agent to the amount of respiratory stimulant may range from about 1:100, 1:95, 1:90, 1:85, 1:80, 1:75, 1:70, 1:65, 1:60, 1:55, 1:50, 1:45, 1:40, 1:35, 1:30, 1:25, 1:20, 1:15, 1:10, 1:9, 1:8, 1:7, 1:6, 1:5, 1:4, 1:3, 1:2, or 1:1 w/w to about 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, or 2:1 w/w.

The mode of administration and dosage forms is closely related to the therapeutic amounts of the compounds or compositions which are desirable and efficacious for the given treatment application.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients.

In one embodiment, the formulation is an intravenous formulation having a long duration of effect. In another embodiment, the formulation contains one of the drugs in an intravenous form, and the other drug in an oral form. In yet a further embodiment, both drugs are in an oral dosage form. In a particular aspect of this further embodiment, both drugs are compounded into a single oral dosage form. In an aspect of this embodiment, the drugs are inseparable from the single oral dosage form by conventional means. In this aspect, the chemoreceptor stimulation of respiratory stimulant opposes the respiratory depressant effect of the therapeutic agent, in particular when the therapeutic agent is an opioid. Thus, the analgesic effect of the opioid acting through the mu receptor is not antagonized by the chemoreceptor activity of the respiratory stimulant.

The oral dosage forms described herein include but are not limited to tablets, caplets, gelcaps and capsules, as well as anal suppositories and vaginal suppositories. To prepare such pharmaceutical dosage forms, one or both of the drugs may be mixed with a pharmaceutical carrier according to conventional pharmaceutical compounding techniques. Similarly, each drug may be mixed with a different carrier, and then assembled into a single oral dosage form. The carrier may take a wide variety of forms depending on the form of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques. Further, as discussed below, the oral dosage forms may be in an immediate release or controlled release formulation.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Treatment methods disclosed herein using formulations suitable for oral administration may be presented as discrete units such as capsules, cachets, tablets, or lozenges, each containing a predetermined amount of the therapeutic agent and/or respiratory stimulant as, for example, a powder or granules. Optionally, a suspension in an aqueous liquor or a nonaqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

Syrup may be made by adding the therapeutic agent and respiratory stimulant to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the therapeutic agent and/or respiratory stimulant with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the therapeutic agent and/or respiratory stimulant in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations disclosed herein may further include one or more accessory ingredient(s) selected from, for example, diluents, buffers, flavoring agents, binders, disintegrants, surface active agents, thickeners, lubricants, preservatives (including antioxidants), and the like.

In one embodiment, the present compositions include a compounded drug of a chemoreceptor respiratory stimulant(s) in combination with an opioid receptor agonist, such as hydrocodone.

The formulations disclosed herein can have immediate release, sustained/controlled release, delayed-onset release or any other release profile known to one skilled in the art. A "controlled release formulation" is a formulation which is designed to slowly release a therapeutic agent in the body over an extended period of time, whereas an "immediate release formulation" is a formulation which is designed to quickly release a therapeutic agent in the body over a shortened period of time. Similarly, in a multiparticulate or layered formulation, there may be both controlled release particles or layers and immediate release particles or layers.

In some cases the immediate release formulation may be coated such that the therapeutic agent is only released once it reached the desired target in the body (e.g. the stomach). This may result in a "delayed release formulation."

As used herein, the term "controlled release" refers to the in vivo release of the therapeutic agent and/or respiratory stimulant from a dosage form in a controlled manner over an extended period of time. For example, a controlled release oral dosage form can release an opioid, e.g., over a 5 to 24 hour interval. As used herein, the terms "sustained release" and "controlled release" are synonymous. In a particular embodiment, the controlled release formulation provides a time to the maximum plasma concentration of therapeutic agent (Tmax) at a time point 3 to 4 times later than the Tmax provided by an equivalent dose of a reference immediate release formulation of the drugs. In an embodiment of the oral dosage form, the Tmax provided by the sustained release formulation occurs at from about 2 to about 8 hours, from about 3 to about 7 hours or from about 4 to about 6 hours after oral administration. Controlled release formulations may be found in U.S. Pat. No. 8,518,443, the entire contents of which are hereby incorporated by reference.

There are multiple ways in which a controlled release may be achieved. Two particular examples of effecting controlled release are by (a) incorporating the therapeutic agent and/or the respiratory stimulant into a controlled release matrix or (b) adding a controlled release coating or layer to delay or regularize the release of the ingredient in the dosage form (or part of the dosage form).

In one embodiment, controlled release is obtained by mixing the therapeutic agent and/or the respiratory stimulant into a matrix comprising a controlled-release material to effect release of the therapeutic agent or respiratory stimulant in a controlled manner.

A non-limiting list of suitable controlled-release materials which may be included in a controlled-release matrix disclosed herein includes hydrophilic and/or hydrophobic materials, such as gums, cellulose ethers, acrylic resins, protein derived materials, waxes, shellac, and oils such as hydrogenated castor oil, hydrogenated vegetable oil. However, any pharmaceutically acceptable hydrophobic or hydrophilic controlled-release material which is capable of imparting controlled-release of either the therapeutic agent or the respiratory stimulant may be used in accordance with the present specification. Controlled-release polymers include alkylcelluloses such as ethylcellulose, acrylic and methacrylic acid polymers and copolymers, and cellulose ethers, especially hydroxyalkylcelluloses (especially hydroxypropylmethylcellulose) and carboxyalkylcelluloses. Acrylic and methacrylic acid polymers and copolymers include methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid) (an hydride), polymethacrylate, polyacrylamide, poly(methacrylic acid anhydride), and glycidyl methacrylate copolymers. Certain embodiments utilize mixtures of any of the foregoing controlled-release materials in the matrices disclosed herein.

The matrix also may include a binder. In such embodiments, the binder preferably contributes to the controlled-release of the therapeutic agent and/or the respiratory stimulant from the controlled-release matrix. In one embodiment, the binder may include natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax.

In addition to the above ingredients, a controlled-release matrix may also contain suitable quantities of other materials, e.g., diluents, lubricants, binders, granulating aids, colorants, flavorants and glidants that are conventional in the pharmaceutical art. Controlled release matrices may be obtained with melt-extrusion techniques.

The controlled-release formulations disclosed herein preferably slowly release the therapeutically active agent, e.g., when ingested and exposed to gastric fluids, and then to intestinal fluids. The controlled-release profile of melt-extruded formulations can be altered, for example, by varying the amount of controlled-release material, by varying the amount of plasticizer relative to other matrix constituents, hydrophobic material, by the inclusion of additional ingredients or excipients, by altering the method of manufacture, etc.

The oral dosage forms disclosed herein may optionally be coated with one or more coatings suitable for the regulation of release or for the protection of the formulation. In one embodiment, coatings are provided to permit either pH-dependent or pH-independent release, e.g., when exposed to gastrointestinal fluid. When a pH-independent coating is desired, the coating is designed to achieve optimal release regardless of pH-changes in the environmental fluid, e.g., the GI tract. Other preferred embodiments include a pH-dependent coating that releases the therapeutic agent and/or respiratory stimulant in desired areas of the gastrointestinal (GI) tract, e.g., the stomach or small intestine, such that an absorption profile is provided which is capable of providing at least about twelve hour and preferably up to twentyfour hour analgesia to a patient. It is also possible to formulate compositions which release a portion of the dose in one desired area of the GI tract, e.g., the stomach, and release the remainder of the dose in another area of the GI tract, e.g., the small intestine.

Formulations disclosed herein that utilize pH-dependent coatings may also impart a repeat-action effect whereby unprotected drug is coated over an enteric coat and is released in the stomach, while the remainder, being protected by the enteric coating, is released further down the gastrointestinal tract. Coatings which are pH-dependent may be used in accordance with the present specification include a controlled release material such as, e.g., shellac, cellulose acetate phthalate (CAP), polyvinyl acetate phthalate (PVAP), hydroxypropyl methylcellulose phthalate, and methacrylic acid ester copolymers, zein, and the like.

In another embodiment, a stabilized solid controlled dosage form is disclosed comprising a therapeutic agent coated with a hydrophobic controlled release material selected from (i) an alkylcellulose; (ii) an acrylic polymer; or (iii) mixtures thereof. The coating may be applied in the form of an organic or aqueous solution or dispersion.

In certain embodiments, the controlled release coating is derived from an aqueous dispersion of the hydrophobic controlled release material. The coated substrate containing the opioid(s) (e.g., a tablet core or inert pharmaceutical beads or spheroids) is then cured until an endpoint is reached at which the substrate provides a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. These formulations are described in detail in U.S. Pat. Nos. 5,273,760 and 5,286,493, hereby incorporated by reference. Other examples of controlled-release formulations and coatings which may be used in accordance with the present specification include U.S. Pat. Nos. 5,324,351; 5,356,467, and 5,472,712, hereby incorporated by reference in their entirety.

In preferred embodiments, the controlled release coatings include a plasticizer such as those described herein below.

Coatings using Alkylcelluloses: Cellulosic materials and polymers, including alkylcelluloses are controlled release materials well suited for coating the substrates, e.g., beads, tablets, etc. according to the present specification. Simply by way of example, one preferred alkylcellulosic polymer is ethylcellulose, although the artisan will appreciate that other cellulose and/or alkylcellulose polymers may be readily employed, singly or on any combination, as all or part of a hydrophobic coatings according to the present specification. Exemplary commercially available alkylcelluloses include AQUACOAT® (FMC Corp., Philadelphia, Pa., U.S.A.) or SURELEASE® (Colorcon, Inc., West Point, Pa., U.S.A.).

Coatings using Acrylic Polymers: In one embodiment, the controlled release material includes controlled-release coating is a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, am ino-alkyl methacrylate copolymer, poly(methacrylic acid anhydride), and glycidyl methacrylate copolymers.

In certain preferred embodiments, the acrylic polymer is comprised of one or more ammonia methacrylate copolymers. Ammonia methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonia methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present specification. For example, there are a family of copolymers synthesized from diethyl-aminoethyl methacrylate and other neutral methacrylic esters, also known as methacrylic acid copolymer or polymeric methacrylates, commercially available as EUDRAGIT® from Rohm Tech, Inc. There are several different types of EUDRAGIT®. For example, EUDRAGIT® E is an example of a methacrylic acid copolymer which swells and dissolves in acidic media. EUDRAGIT® L is a methacrylic acid copolymer which does not swell at about pH<5.7 and is soluble at about pH>6. EUDRAGIT® S does not swell at about pH<6.5 and is soluble at about pH>7. EUDRAGIT® RL and EUDRAGIT® RS are water swellable, and the amount of water absorbed by these polymers is pH-dependent, however, dosage forms coated with EUDRAGIT® RL and RS are pH-independent.

In certain embodiments, the acrylic coating comprises a mixture of two acrylic resin lacquers commercially available from Rohm Pharma under the Tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. [125] The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids.

The EUDRAGIT® RL/RS dispersions disclosed herein may be mixed together in any desired ratio in order to ultimately obtain a controlled-release formulation having a desirable dissolution profile. Desirable controlled-release formulations may be obtained, for instance, from a retardant coating derived from 100% EUDRAGIT® RL, 50% EUDRAGIT® RL and 50% EUDRAGIT® RS, and 10% EUDRAGIT® RL: EUDRAGIT® 90% RS. Of course, one skilled in the art will recognize that other acrylic polymers may also be used, such as, for example, EUDRAGIT® L.

Optional Plasticizers: In some embodiments, the inclusion of an effective amount of a plasticizer in the controlled-release material will further improve the physical properties of the controlled-release coating. For example, because ethylcellulose has a relatively high glass transition temperature and does not form flexible films under normal coating conditions, it is preferable to incorporate a plasticizer into an ethylcellulose coating containing controlledrelease coating before using the same as a coating material.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose disclosed herein.

Examples of suitable plasticizers for the acrylic polymers disclosed herein include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose disclosed herein.

It has further been found that the addition of a small amount of talc to the controlled release coating reduces the tendency of the aqueous dispersion to stick during processing, and acts as a polishing agent.

In one embodiment, the dosage forms may include an amount of an immediate release therapeutically active agent for prompt therapeutic effect. The immediate release therapeutically active agent may be incorporated, e.g., as separate pellets within a gelatin capsule, or may be coated on the surface of, e.g., a tablet, or beads or particles.

In one embodiment, the oral dosage form includes coated spherical particles comprising one or more of the therapeutic agent or the respiratory agents. Spherical particles may be made with the inclusion of a spheronising agent. Spheronising agents which may be used to prepare the oral formulations disclosed herein include any art-known spheronising agent. Cellulose derivatives are preferred, and microcrystalline cellulose is especially preferred. A suitable microcrystalline cellulose is, for example, the material sold as AVICEL PH 101™ (FMC Corporation). The spheronising agent is preferably included as about 1 to about 99% of the matrix bead by weight.

These spherical particles may be coated to change the release profile of the therapeutic agent or the respiratory stimulant, or both. For instance, the coated spherical particles include a population of particles coated with an immediate release composition. In one embodiment, there may be two populations of coated spherical particles, the first population of particles being coated with an extended release composition, and the second population being coated with an immediate release population.

Further, coated particles may be obtained using powder layering techniques. One method of producing controlled release bead formulations suitable for about 24-hour administration is via powder layering. U.S. Pat. No. 5,411,745, hereby incorporated by reference in its entirety, teaches preparation of 24-hour morphine formulations prepared via powder layering techniques utilizing a processing aid consisting essentially of hydrous lactose impalpable. The powder-layered beads are prepared by spraying an aqueous binder solution onto inert beads to provide a tacky surface, and subsequently spraying a powder that is a homogenous mixture of morphine sulfate and hydrous lactose impalpable onto the tacky beads. The beads are then dried and coated with a hydrophobic material such as those described hereinabove to obtain the desired release of drug when the final formulation is exposed to environmental fluids. An appropriate amount of the controlled release beads are then, e.g. encapsulated to provide a final dosage form which provides effective plasma concentrations of morphine for about 12 hours.

In one embodiment, the present oral dosage form is formulated as a layered tablet. For instance, a layered table may include a central core, one or more intermediate layers, and a surface layer.

The central core may include the therapeutic agent and/or the respiratory stimulant at either a sustaining dosage, or at a bolus dosage. The sustaining dosage is intended to maintain or decrease the blood concentration of either or both of the therapeutic agent and respiratory stimulant, but not to increase the blood concentration of the drug. In one embodiment, a sustaining dosage is equal to or less than 30% of either the therapeutic agent or the respiratory stimulant. In one embodiment, the sustaining dosage is less than 10%, less than 15%, less than 20%, less than 25%, or less than 30% of the drug in the layered tablet dosage form.

The bolus dosage is intended to be an increased dose of either or both of the therapeutic agent and respiratory stimulant. For instance, a bolus dosage may be at least 30% to at least 100% of the amount of drug found in the rest of the layered tablet dosage form. In one embodiment, the bolus dose is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99%, or at least 100% of either the therapeutic agent or the respiratory stimulant found in the layered tablet dosage form.

In another embodiment, the bolus dosage is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99%, or at least 100% of the therapeutic agent and the respiratory stimulant found in the layered tablet dosage form.

Optionally, the layered tablet may include intermediate layers. The intermediate layers may be formulated for immediate release or controlled release. In one embodiment, the intermediate layer contains a bolus dosage of one or both of the therapeutic agent and the respiratory stimulant. For instance, a bolus dosage in an intermediate may be at least 30% to at least 100% of the amount of drug found in the rest of the layered tablet dosage form. In one embodiment, the bolus dose is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99%, or at least 100% of either the therapeutic agent or respiratory stimulant found in the layered tablet dosage form. In another embodiment, the bolus dosage in the sustaining layer is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99%, or at least 100% of the therapeutic agent and the respiratory stimulant found in the layered tablet dosage form.

In another embodiment, an intermediate layer contains a sustaining dose of either the therapeutic agent or the respiratory stimulant. In one aspect, the sustaining dosage in an intermediate layer may be equal to or less than 30% of either the therapeutic agent or the respiratory stimulant. In one embodiment, the sustaining dosage is less than 10%, less than 15%, less than 20%, less than 25%, or less than 30% of the drug in the layered tablet dosage form.

In yet another embodiment, the intermediate layers are measured according to their thickness. For instance, if a tablet is a flattened ovoid shape, the intermediate layer may have a thickness of 5%, 10%, 15%, 20%, 25%, 30%, 35%, 40%, 45%, or 50% of the small diameter of the oval footprint of the tablet.

The layered tablet also includes a surface layer. The surface layer may include both the therapeutic agent and the respiratory stimulant, neither the therapeutic agent or the respiratory stimulant, or either the therapeutic agent or the respiratory stimulant. In one embodiment, the surface layer includes the therapeutic agent, but not the respiratory stimulant. The surface layer may include a bolus dosage of the therapeutic agent, such as at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99%, or at least 100% of the therapeutic agent found in the layered tablet dosage form. In one embodiment, the surface layer contains neither the therapeutic agent nor the respiratory stimulant, and is instead a coating layer, such as an enteric coating.

In between layers, one or more inert or coating layers may be applied to periodically delay or control the release of the therapeutic agent, the respiratory stimulant, or both the therapeutic agent and respiratory stimulant. The inert layers by definition do not include either the therapeutic agent or the respiratory stimulant. The coating layers may include either the therapeutic agent or the respiratory stimulant, but most importantly are formulated to delay release of the drugs encapsulated by the coating layers until the designated physiological conditions are met such that the coating dissolves or is worn away.

This inert layer serves as a delay mechanism to separate the release of different layers having the therapeutic agent and/or the respiratory stimulant. These inert layers may be made of pharmaceutically acceptable carriers, binders, and other fillers, as discussed above.

In a particular embodiment, the layered tablet dosage form includes a core having a bolus dosage of both the therapeutic agent and the respiratory stimulant in a controlled release matrix, and a surface layer consisting of an enteric coating, and having neither the therapeutic agent or the respiratory stimulant. In this embodiment, 100% of the drugs are included in the core.

In another embodiment, the layered tablet dosage form includes a core having core having a bolus dosage of both the therapeutic agent and the respiratory stimulant in a controlled release matrix, a first intermediate layer including the respiratory stimulant, a second intermediate layer having both the therapeutic agent and the respiratory stimulant, and a surface layer that is an enteric coating. In this embodiment, the amount of therapeutic agent in the core may be about 30-70% of the total therapeutic agent in the layered tablet and the amount of respiratory stimulant in the core may be about 30-60% of the total respiratory stimulant in the layered tablet. Thus, the remainder of the therapeutic agent is found in the second intermediate layer, and the remainder of the respiratory stimulant may be found in divided between the first and second intermediate layers.

In yet a further embodiment, the layered tablet dosage form includes from the inside out: a core having a bolus dosage of the respiratory stimulant, an inert layer, an intermediate layer having the therapeutic agent and/or the respiratory stimulant in an extended release form, an intermediate layer having the respiratory stimulant, and a surface layer that includes a bolus dosage of the therapeutic agent. In one aspect of this embodiment, the therapeutic agent is divided between the intermediate layer and the surface layer, and the respiratory stimulant is divided between the core, the intermediate layer (optionally), and the surface layer.

In one embodiment, the respiratory stimulant is included with or follows a layer having the therapeutic agent. This ensures that the respiratory stimulant counteracts the side-effects of the therapeutic agent. In the layered tablet dosage form, each layer may have a different ratio of therapeutic agent and respiratory stimulant. Techniques and compositions for making tablets (compressed and molded), capsules (hard and soft gelatin) and pills are also described in Remington's Pharmaceutical Sciences, (Arthur Osol, editor), 1553-1593 (1980), incorporated by reference herein.

In some embodiments, any of the compositions disclosed herein will comprise therapeutic agent and the respiratory stimulant disclosed herein, in any form or embodiment as described herein. In some embodiments, any of the compositions disclosed herein will comprise of a compound disclosed herein, in any form or embodiment as described herein. In some embodiments, of the compositions disclosed herein will consist essentially of a compound disclosed herein, in any form or embodiment as described herein. In some embodiments, the term "comprise" refers to the inclusion of the indicated therapeutic agent and the respiratory stimulant, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is one or both of the therapeutic agent and the respiratory stimulant, however, other compounds may be included which are for stabilizing, preserving, etc. the formulation, but are not involved directly in the therapeutic effect of the indicated therapeutic agent or the respiratory stimulant. In some embodiments, the term "consisting essentially of" may refer to components which facilitate the release of the therapeutic agent and/or the respiratory stimulant. In some embodiments, the term "consisting" refers to a composition, which contains the therapeutic agent, the respiratory stimulant, and a pharmaceutically acceptable carrier or excipient.

A method for treating pain: In one embodiment, the present compositions are used for the treatment of acute and/or chronic pain. For instance, the compositions may be administered as a method of treating pain, or used in manufacture of a pharmaceutical composition for the treatment of pain. As used herein, the phrases "treatment of pain" or "treating pain" refer to the amelioration of pain or the cessation of pain or avoidance of the onset of pain in a patient. In one embodiment the amelioration of pain is pain resulting from: complex regional pain syndrome, postoperative pain, rheumatoid arthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, cough, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. In one embodiment, the treatment is of acute pain, such as pain lasting less than three months. In one aspect, the treatment of acute pain is with a short term regimen of opioid analgesics at a comparatively high dose. In such aspect, the treatment may be at such a high dose that respiratory suppression is likely if the opioid analgesic were administered without a respiratory stimulant. In another embodiment, the treatment is of chronic pain, such as pain lasting more than three months. In one aspect, the treatment is of chronic pain resulting from cancer, rheumatoid arthritis, or back pain. In such aspect, the patient may already have a tolerance for opioid analgesic medications, and therefore, a high dosage of opioid analgesic may be needed to provide adequate pain relief. Alternatively, in such aspect, the patient may be particularly sensitive to the respiratory suppressive effects of opioid analgesics (or those of other therapeutic agents described herein), for instance where the patient is elderly. In such an instance, the respiratory stimulant would be needed to avoid potential consequences of respiratory suppression. Finally, the present methods are useful to treat other types of pain, such as break through pain. The present methods allow for treatment with a significantly increased dosage of therapeutic agent, while simultaneously addressing the needs of the patient for appropriate pain relief in a safe outpatient manner.

The term "effective pain management" means an objective evaluation of a human patient's response (pain experienced versus side effects) to analgesic treatment by a physician as well as subjective evaluation of therapeutic treatment by the patient undergoing such treatment. One skilled in the art will understand that effective analgesia will vary according to many factors, including individual patient variability. Thus, in one embodiment, the treatment of pain entails effective pain management.

In one embodiment, the pharmaceutical compositions disclosed herein reduces the symptoms of pain by at least 95%, at least 90%, at least 85%, at least 80%, at least 75%, at least 70%, at least 65%, at least 60%, at least 55%, at least 50%, at least 45%, at least 40%, at least 35%, at least 30%, or at least 25% as measured by objective or subjective criteria, or a combination of objective and subjective criteria as recognized in the art.

The present compositions are particularly advantageous in patient care because there would be no decrease in the analgesic properties of the opioid, which actually may enhance patient adherence with opioid prescriptions. Patients would not be able to appreciate a decrease in efficacy for analgesia. The individual would still be able to reach the euphoric "high" so desired but they would be alive. By combining the opioid agonist with the inseparable respiratory stimulant or stimulants, the predicament of adequately treating pain while maintaining patient safety is satisfied. The death rate would predictably decrease while treatment of pain would improve.

To effectively treat pain, the plasma concentration of the therapeutic agent must be an effective plasma concentration to decrease pain. While the blood plasma concentration of each therapeutic agent may vary, effective blood plasma concentrations for opioid agonists have been studied. For instance, a maximum plasma concentration (Cmax) of hydrocodone bitartrate after the administration of 15 mg hydrocodone to a human subject may range from about 1 to 40 µg/ml, depending on the formulation of the dosage (see, e.g., U.S. Pat. No. 7,943,174, the entire contents of which are hereby incorporated by reference). Similarly, the term "Tmax" denotes the time to maximum plasma concentration (Cmax), and will differ depending on whether a formulation is "immediate release" or "controlled release."

The effectiveness of any particular plasma concentration may differ from subject to subject, but in a particular embodiment, the effective plasma concentration is at least about 5 µg/ml, 8 µg/ml, 10 µg/ml, or 12 µg/ml after a single dose of 15 mg hydrocodone bitartrate.

In a further embodiment, the effective plasma concentration is at least 1 µg/ml, at least 2 µg/ml, at least 3 µg/ml, at least 4 µg/ml, at least 5 µg/ml, at least 6 µg/ml, at least 7 µg/ml, at least 8 µg/ml, at least 9 µg/ml, at least 10 µg/ml, at least 11 µg/ml, at least 12 µg/ml, at least 13 µg/ml, at least 14 µg/ml, at least 15 µg/ml, at least 16 µg/ml, 17 µg/ml, at least 18 µg/ml, at least 19 µg/ml, at least 20 µg/ml, at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 800 µg/ml or more µg/ml.

Similarly, in the formulation, the respiratory stimulant must be at a concentration which is suitable to stimulate respiration. In one embodiment, the effective blood concentration of doxapram used to increase minute volume (VE) (which is a measure based on tidal volume and respiratory rate) in humans ranges from about 1 to about 3 µg/ml. In one aspect, the effective blood concentration is about 1.5 to about 2 µg/ml. Measured another way, the effective blood concentration of doxapram in humans ranges from about 4 to about 5 µM. This is similar to rats, and is likely conserved across species.

The controlled release formulations disclosed herein and the immediate release control formulations are dose proportional. In such formulations, the pharmacokinetic parameters (e.g. the "area under the curve", AUC, and Cmax) increase linearly from one dosage strength to another. Therefore the pharmacokinetic parameters of a particular dose can be inferred from the parameters of a different dose of the same formulation.

A method of administering anesthesia: In one embodiment, the present compositions are used in the administration of anesthesia. For instance, the compositions may be administered as an anesthetic, or used in manufacture of an anesthetic pharmaceutical composition. In one aspect of this embodiment, the formulation is an intravenous formulation. In another aspect of this embodiment, one drug is administered intravenously and the other drug is simultaneously administered orally. As with the treatment of pain, the amount of therapeutic agent must be sufficient to provide effective anesthesia, and the amount of respiratory stimulant must be sufficient to stimulate respiration.

The differences between the amount of therapeutic agent needed to treat pain and the amount of therapeutic agent to induce a desired level of anesthesia again will depend on the patient, the patient's condition and the therapeutic agent to be administered. Such differences are recognized by artisans skilled in the treatment of pain and anesthesiologists.

A method of treating obstructive sleep apnea: In one embodiment, the present compositions are used for the treatment of pain while simultaneously treating obstructive sleep apnea. Opioids and other respiratory depressants exacerbate preexisting sleep disorder breathing in the perioperative method. Thus, administration of a respiratory stimulant may mitigate this effect. The effect of doxapram on the severity of obstructive sleep apnea (OSA) has been evaluated in a small study using four subjects. Doxapram decreased the duration and severity of oxyhemoglobin desaturation events, with no effect on the number of desaturations or time spent in NREM and REM sleep. Unfortunately, doxapram also increased blood pressure, which is undesirable in people with a disease known to cause hypertension. The data suggest that increasing respiratory drive chemically, presumably via peripheral chemoreceptors, is a rational approach to treating sleep disordered breathing (SDB) in the perioperative setting. However, the utility of the present compositions extends beyond the perioperative sphere. For instance, the present compositions may be useful where a chronic pain patient cannot take opioids due to the high potential for obstructive sleep apnea which resulted from another condition (e.g., diabetes, obesity etc.). Thus, the present disclosure contemplates the use of the present compositions in the manufacture of a medicament for the treatment of obstructive sleep apnea. In a particular aspect of this embodiment, the formulation is an oral formulation.

In yet a further embodiment, the present compositions may be used in a method for preventing or deterring abuse of the therapeutic agent. In one aspect, the method for preventing or deterring abuse is a method for deterring abuse of opioid analgesic agents. In one embodiment, the present compositions are administered to a patient with a history of abuse or a likelihood of abuse. A patient having a likelihood of abuse is a patient with a known familial history of abuse, a patient with a known history of abuse of another substance, or a patient with diagnosed or acknowledged psychological tendencies or sensitivities towards addiction.

An opioid abuser tends to take an increased dosage of opioid in a short period to obtain a "high." Typically the higher dosage is obtained by either increasing the total amount of opioid taken (e.g., by increasing the number of pills) or by modifying an extended release medication (by crushing or other means) to ensure that the entire dose of opioid analgesic is delivered to the addict in an immediate release form. The present compositions deter abuse in a two-fold manner: First, if an increased amount of the present compositions having an opioid analgesic are taken, while the patient may reach their "high" because the respiratory suppressive effects are minimized or eliminated, the other uncomfortable side effects of opioid analgesics become prevalent (such as itching, dry mouth etc.) changing the experience of the "high" from a purely pleasurable sensation to a personally uncomfortable experience. The changed quality of the euphoric experience deters the abuser from attempting to reach the same state again. Second, when the dosage forms disclosed herein are crushed or modified from an extended release to an immediate release form by an abuser, the presence of the respiratory stimulant in the modified formulation again changes the quality of the euphoric experience to a less pleasant state and allows the other unpleasant side effects of the therapeutic agent to be felt, again deterring future abuse.

In one embodiment, a method for treating drug abuse disclosed herein comprising administration of the present composition to an addict or drug abuser. In one aspect, the addict or drug abuser is an opioid addict. In yet a further aspect, the present composition replaces a dose of opioid analgesic administered as a replacement therapy for the addict or drug abuser's drug of choice. In yet another aspect, the replacement therapy is methadone, and/or the drug of choice is heroin. In such an aspect, the present compositions may contain a combination of methadone and a respiratory stimulant in oral dosage form.

As used herein, the terms "patient" or "animal" include, but are not limited to, mammals. Mammals of particular interest include a cow, monkey, horse, sheep, pig, chicken, turkey, quail, cat, dog, mouse, rat, rabbit, hamster, guinea pig, or human.

As used herein, the term "steady state" refers to a state in which the amount of the therapeutic agent reaching the system is approximately the same as the amount of the drug leaving the system. Thus, at steady state, the patient's body eliminates the therapeutic agent at approximately the same rate that the drug becomes available to the patient's system through absorption into the bloodstream. In some instances, steady state is not achieved until after several sequential administrations of a dosage of the therapeutic agent at specified time intervals.

In an embodiment, in instances in which each of the therapeutics themselves are administered, without limitation, as individual or separate dosage forms (e.g., capsules or tablets), the kit comprises, without limitation, each of the therapeutics making up the composition disclosed herein, along with instructions for use. In an additional embodiment, the therapeutic components, without limitation, may be packaged in any manner suitable for administration, so long as the packaging, when considered along with the instructions for administration, without limitation, clearly indicates the manner in which each of the therapeutic components is to be administered. In a further embodiment, each of the therapeutics or a combination of such therapeutics may, without limitation, be combined into a single administrable dosage form such as a capsule, tablet, or other solid or liquid formulation. The therapeutic can be provided to an individual in a package. The package can be a container, for instance, without limitation, a bottle, a canister, a tube or other enclosed vessel. The package can also be a packet, such as a blister pack. In an embodiment, the individual or separate dosage is in the form of a blister pack. In an aspect of this embodiment, a blister pack is a term for several types of pre-formed plastic packaging used for small consumer goods, foods, and for pharmaceuticals. In a further embodiment, a blister pack is comprised of a cavity or pocket made from a formable web, usually a thermoformed plastic and typically includes a backing of paperboard or a lidding seal of aluminum foil or plastic. In a further embodiment, a blister that folds onto itself is a clamshell. In an aspect of this embodiment, a blister pack is commonly used as unit-dose packaging for pharmaceutical tablets, capsules or lozenges. In an embodiment, a blister pack can provide barrier protection for shelf life requirements, and a degree of tamper resistance and can be used for packing physician samples of cancer therapeutic products or for Over The Counter (OTC) products in the pharmacy.

Aspects of the Invention

In one aspect, the invention includes a pharmaceutical composition comprising a therapeutic agent and a respiratory stimulant. In another aspect, the invention includes a therapeutic agent that is an analgesic, a benzodiazepine, barbiturate, an antihistamine, or any combination thereof. In another aspect, the invention includes an analgesic that is an opioid receptor agonist or a non-steroidal anti-inflammatory agent. In another aspect, the opioid receptor agonist is an opioid mu or kappa receptor agonist.

In another aspect, the opioid mu receptor agonist is selected from the group consisting of DAMGO ([D-Ala2, NMe-Phe4, Gly-ol5]-enkephalin), Endomorphin-1 (Endomorphin-1 TyrPro-Trp-Phe-NH2), Endomorphin-2 (Tyr-Pro-Phe-Phe-NH2), Fenanyl citrate (N-Phenyl-N-[1(2-phenylethyl)-4-piperidinyl]propanamide citrate), loperamide hydrochloride (4-(4Chlorophenyl)-4-hydroxy-N,N-dimethyl-α,α-diphenyl-1-piperidinebutanamide hydrochloride), metazinol hydrochloride (3-(3-Ethylhexahydro-1-methyl-1H-azepin-3-yl)phenol hydrochloride), oxycodone hydrochloride ((5α)-4,5-Epoxy-14-hydroxy-3-methoxy-17methylmorphinan-6-one hydrochloride), PL 017 (PL 017 Tyr-Pro-N-Methyl-Phe-D-Pro-NH2), and sinomenine hydrochloride (9α,13α,14α-7,8-Didehydro-4-hydroxy-3,7-dimethoxy-17methylmorphinan-6-one hydrochloride) and pharmaceutically acceptable salts thereof.

In another aspect, the opioid kappa receptor agonist is selected from the group consisting of 6'-Guanidinonaltrindole (6'-GNTI), 8-Carboxamidocyclazocine, Alazocine, Asimadoline, Bremazocine, Butorphan, Butorphanol, BRL-52537, CR665, Cyclazocine, Cyclorphan, Difelikefalin (CR845), Diprenorphine, dynorphin A, dynorphin B, big dynorphin, Eluxadoline, Enadoline, Erinacine E, Etorphine, GR-89696, HS665, HZ-2, Ibogaine, ICI-204,448, ICI-199, 441, Ketamine, Ketazocine, Levallorphan, Levomethorphan, Levorphanol, LPK-26, MB-1C—OH, Menthol, Metazocine, Morphine, N-MPPP, Nalbuphine, Nalfurafine, Nalmefene, Nalodeine, Nalorphine, Niravoline, Norbuprenorphine, Norbuprenorphine-3-glucuronide, Noribogaine; biased ligand, Oxilorphan, Oxycodone, Pentazocine, Phenazocine, Proxorphan, RB-64 (22-thiocyanatosalvinorin A), Salvinorin A, 2-Methoxymethyl salvinorin B, Samidorphan, Spiradoline, Tifluadom, U-50,488, U-54,494A, U-69, 593, Xorphanol, and Nalfurafine and pharmaceutically acceptable salts thereof.

In another aspect the opioid receptor agonist is selected from the group consisting of alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levallorphan, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propiram, propoxyphene, propylhexedrine, sufentanil, tilidine, tramadol, pharmaceutically acceptable salts of the foregoing, and/or mixtures of any two or more of the foregoing.

In another aspect, wherein the opioid receptor agonist is hydrocodone, morphine, hydromorphone, oxycodone, codeine, levorphanol, meperidine, methadone, oxymorphone, buprenorphine, fentanyl, dipipanone, heroin, tramadol, etorphine, dihydroetorphine, dihydrocodeine, dihydromorphine, butorphanol, levorphanol, pharmaceutically acceptable salts of the foregoing, and mixtures of any two or more of the foregoing.

In another aspect, the benzodiazepine is selected from the group consisting of: Alprazolam; Bentazepam; Bretazenil; Bromazepam; Brotizolam; Camazepam; Chlordiazepoxide; Cinolazepam; Clobazam; Clonazepam; Clorazepate; Clotiazepam; Cloxazolam; Delorazepam; Deschloroetizolam; Diazepam; Diclazepam; Estazolam; Ethyl carfluzepate; Etizolam; Ethyl loflazepate; Flubromazepam; Flunitrazepam; Flurazepam; Flutoprazepam; Halazepam; Ketazolam; Loprazolam; Lorazepam; Lormetazepam; Medazepam; Midazolam; Nimetazepam; Nitrazepam; Nordiazepam; Oxazepam; Phenazepam; Pinazepam; Prazepam; Premazepam; Pyrazolam; Quazepam; Temazepam; Tetrazepam; Triazolam; DMCM; Flumazenil; Eszopiclon; Zaleplon; Zolpidem; Zopiclone, pharmaceutically acceptable salts of the foregoing, and/or In another aspect, the barbiturate is selected from the group consisting of allobarbital, alphenal, aprobarbital, brallobarbital, cyclobarbital, methylpehnobarbital, talbutal, thiamylal, methohexital (BREVITAL®), thiamyl (SURITAL®), thiopental (PENTOTHAL®), amobarbital (AMYTAL®), pentobarbital (NEMBUTAL®), secobarbital (SECONAL®), butalbital (FIORINA®), butabarbital (BUTISOL®), phenobarbital (LUMINAL®), and mephobarbital (MEBARAL®) and pharmaceutically acceptable salts thereof.

In another aspect, the antihistamine is selected from the group consisting of: Acrivastine, Azelastine, Bilastine, Brompheniramine, Buclizine, Bromodiphenhydramine, Carbinoxamine, Cetirizine, Chlorpromazine, Cyclizine, Chlorphenamine, Chlorodiphenhydramine, Clemastine, Cyproheptadine, Desloratadine, Dexbrompheniramine, Dexchlorpheniramine, Dimenhydrinate, Dimetindene, Diphenhydramine, Doxylamine, Ebastine, Embramine, Fexofenadine, Hydroxyzine, Levocetirizine, Loratadine, Meclozine, Mirtazapine, Olopatadine, Orphenadrine, Phenindamine, Pheniramine, Phenyltoloxamine, Promethazine, Pyrilamine, Quetiapine, Rupatadine, Tripelennamine, Triprolidine, Cimetidine, Famotidine, Lafutidine, Nizatidine, Ranitidine, Roxatidine, Tiotidine, mixtures thereof, and pharmaceutically acceptable salts thereof.

In another aspect, the the non-steroidal anti-inflammatory agent is acetylsalicylic acid (aspirin), celecoxib (CELEBREX™), dexdetoprofen (KERAL™), diclofenac (VOLTAREN™, CATAFLAM™, VOLTAREN-XR™), diflunisal (DOLOBID™), etodolac (LODINE™, LODINE XL™), etoricoxib (ALGIX™), fenoprofen (FENOPRON™, NALFRON™), firocoxib (EQUIOXX™ PREVICOX™), flurbiprofen (URBIFEN™, ANSAID™, FLURWOOD™, FROBEN™), ibuprofen (ADVIL™, BRUFEN™, MOTRIN™, NUROFEN™, MEDIPRENT™, NUPRIN™), indomethacin (INDOCIN™, INDOCIN SR™, INDOCIN IV™), ketoprofen (ACTRON™, ORUDIS™ ORUVAIL™, KETOFLAM™), ketorolac (TORADOL™, SPRIX™, TORADOL IV/IM™, TORADOL IM™). licofelone, lornoxicam (XEFO™), loxoprofen (LOXONIN™, LOXOMAC™, OXENO™), lumiracoxib (PREXIGE™), meclofenamic acid (MECLOMEN™), mefenamic acid (PONSTEL™), meloxicam (MOVALIS™, MELOX™, RECOXA™, MOBIC™), nabumetone (RELAFEN™), naproxen (ALEVE™, ANAPROX™, MIDOL EXTENDED RELIEF™ NAPROSYN™, NAPRELAN™), nimesulide (SULIDE™, NIMALOX™, MESULID™), oxaporozin (DAYPRO™, DAYRUN™, DURAPROX™), parecoxib (DYNASTAT™), piroxicam (FELDENE™), rofecoxib (VIOXX™, CEOXX™, CEEOXX™), salsalate (MONOGESIC™, SALFLEX™, DISALCID™, SALSITAB™), sulindac (CLINORIL™), tenoxicam (MOBIFLEX™), tolfenamic acid (CLOTAM RAPID™, TUFNIL™), and valdecoxib (BEXTRA™).

In another aspect, wherein the respiratory stimulant is doxapram, modafinil, almitrine, AMPAkines, GAL-021, buspirone, mosapride, CX546, CX717, pharmaceutically acceptable salts thereof, or any combination thereof.

In one aspect, the invention includes a respiratory stimulant that is doxapram, modafinil, or almitrine, pharmaceutically acceptable salts thereof, or any combination thereof.

In one aspect, the invention includes a pharmaceutical composition comprising a respiratory stimulant and a therapeutic agent, the respiratory stimulant selected from the group consisting of doxapram and modafinil and the therapeutic agent selected from the group consisting of hydrocodone, oxycodone, hydromorphone, lorazepam, alprazolam, carisprodol, and methocarbamol. In one aspect, the respiratory stimulant is doxapram and the therapeutic agent is selected from the group consisting of hydrocodone, oxycodone, hydromorphone, lorazepam, alprazolam, carisprodol, and methocarbamol. In another aspect, the respiratory stimulant is modafinil and the therapeutic agent is selected from the group consisting of hydrocodone, oxycodone, hydromorphone, lorazepam, alprazolam, carisprodol, and methocarbamol.

In one aspect, the pharmaceutical composition is in the form of an intravenous formulation having a long duration of effect. In another aspect, both the therapeutic agent or the respiratory stimulant are in an oral dosage form. In another aspect, the therapeutic agent and the respiratory stimulant are compounded into a single oral dosage form. In another aspect, the therapeutic agent and the respiratory stimulant are inseparable from the single oral dosage form by conventional means.

In one aspect, the ratio of the amount of therapeutic agent to the amount of respiratory stimulant ranges from 1:100 w/w to 100:1 w/w.

In one aspect, the invention includes an oral dosage form comprising the pharmaceutical composition described above. In another aspect, the oral dosage is in the form of a syrup, a tablet, a caplet, a gelcap, a lozenge, or a capsule. In another aspect, the tablet is a layered tablet. In another aspect, the layered tablet comprises a central core, one or more intermediate layers, and a surface layer. In another aspect, the therapeutic agent is located in at least the surface layer of the oral dosage form. In another aspect, the therapeutic agent is located in at least a core of the oral dosage form. In another aspect, the respiratory stimulant is located in at least a core of the oral dosage form. In another aspect, the therapeutic agent is located in at least a surface layer of the oral dosage form, and the surface layer is formulated for immediate release. In another aspect, the analgesic is located in coated spherical particles. In another aspect, the coated spherical particles include a population of particles coated with an extended release composition. In another aspec, the coated spherical particles include a population of particles coated with an immediate release composition. In another aspect, the respiratory stimulant is also located in coated spherical particles. In another aspect, the dosage form is a capsule. In another aspect, the ratio of the amount of therapeutic agent to the amount of respiratory stimulant ranges from 1:100 w/w to 100:1 w/w.

In one aspect, the invention includes a method for treating pain comprising administering the pharmaceutical composition or the oral dosage form described above to a patient experiencing pain. In another aspect, the invention includes a method of administering anesthesia comprising administering the pharmaceutical composition or the oral dosage form described above to a patient in need thereof. In another aspect, the invention includes a method of treating obstructive sleep apnea comprising administering the pharmaceutical composition or the oral dosage form described above to a patient in need thereof. In another aspect, the invention includes a method of preventing or deterring abuse of the therapeutic agent comprising administering the pharmaceutical composition or the oral dosage form described above to a patient in need thereof. In another aspect, the invention includes a method for treating drug abuse comprising administration of the pharmaceutical composition or the oral dosage form described above to a drug addict or drug abuser.

EXAMPLES

The following non-limiting examples are provided for illustrative purposes only in order to facilitate a more complete understanding of the disclosed subject matter. These examples should not be construed to limit any of the embodiments described in the present specification, including those pertaining to the pharmaceutical compositions, oral dosage forms and methods.

Example 1: Oral Dosage Form with Doxapram

An oral dosage form constructed of an inner core of doxapram followed by alternating layers of doxapram and hydrocodone in a polysucrose gel matrix, which would establish opioid deterrent and respiratory stimulant properties to prevent both abuse and death from respiratory arrest.

If an opioid abuser were to take more oral opioid pills than prescribed or illicitly crush opioid pills for intravenous injection, the unopposed mu receptor activation would lead to pain relief but also other mu receptor effects, and respiratory depression. Without antagonism or other countermeasures, respiratory depression and death could result. The novel new pain drug combination would release a constant ratio of the opioid mu receptor agonist but also the respiratory stimulant drug, doxapram, a centrally acting chemoreceptor. Doxapram does not affect the mu receptors and therefore classifies Doxapram, as predominately a countermeasure to opioid mu receptor effects rather than an antagonist. The respiratory depressant effects of opioids would be countered thus continued treatment of pain with opioids would be safer. Patient lives would be saved. Interestingly, it would then be predicted that compliance to pain medication would improve because treatment pain would continue. As higher levels of opioids are taken, the increased side effects from opioid mu, delta, and kappa activation, would act as a natural deterrent to abuse. The analgesic and euphoric properties would be overcome and less enjoyable with increasing sensations of nausea, vomiting, sexual dysfunction, and cognitive dysfunction.

Example 2: Layered Pill Manufacture and Testing

Characteristics of Doxapram and its metabolites: Doxapram's effect on minute ventilation is from 0 to 10 minutes, with return to baseline by 15 minutes. With 1.5 mg/kg bolus, almost immediate peak reached in serum, around 3 µg/ml. T1/2 of 3.4 hours. With 3.5 mg IV infusion 3.5 mg/kg/hr for 2 hours, the peak plasma concentration of 4.0 µg/ml was reached right after infusion stopped, with T1/2 3.9 hours after stop of infusion. With 300 mg oral administration, plasma detection occurred at 1, 1.5, 2, and 2 hours after ingestion. Peak plasma concentration was 0.96 µg/ml. The oxidized metabolite is AHR 5955, ketodoxapram, which is metabolically active in lambs in a dose dependent fashion.

Pill Composition: Pills having the following compositions are created with two layers, Layer A and Layer B as shown below. Layer A Layer B 1 Doxapram 50 mg+5 mg Hydrocodone Doxapram 250 mg+250 mg HPMC 4000 cP 2 Doxapram 100 mg+5 mg Hydrocodone Doxapram 200 mg+200 mg HPMC 4000 cP 3 Doxapram 150 mg+5 mg Hydrocodone Doxapram 150 mg+150 mg HPMC 4000 cP 4 Doxapram 50 mg Doxapram 250 mg+250 mg HPMC 4000 cP 5 Doxapram 100 mg Doxapram 200 mg+200 mg HPMC 4000 cP 6 Doxapram 150 mg Doxapram 150 mg+150 mg HPMC 4000 cP 7 Doxapram 300 mg None 8 5 mg Hydrocodone Doxapram 300 mg+300 mg HPMC 4000 cP 9 5 mg Hydrocodone 300 mg HPMC 4000 cP 10 5 mg Hydrocodone None.

Layer A components mixed thoroughly until a uniform mixture was achieved, placed in cast and pressed to form pill. The cast was then readjusted to allow for Layer B. Layer B components mixed thoroughly until a uniform mixture was achieved. The fill layer B mixture was then deposited onto the Layer A formed tablet, and then pressed (same pressure as for Layer A) to form two layer pill/tablet.

Simulated Gastric Fluid (SGF) was made by adding 7.0 mL of HCl to 900 mL of deionized water, and then dissolving 2.0 g NaCl and 3.2 g Pepsine (800-2500 U/mg). Deionized water is added until the solution reaches 1,000 ml.

Simulated Intestinal Fluid (SIF) was made by adding 6.8 g of monobasic KH2PO4 (potassium phosphate) in 250 ml of water, and then adding 77 ml of 0.2 N NaOH.

Deionized water is then added until the solution reaches 500 ml. To this solution, 10.0 g of pancreatin is dissolved and the solution was adjust pH to 6.8±0.1 using 0.2 N NaOH or 0.2 N HCl. Deionized water is added until the solution reaches 1,000 ml.

Dissolution Testing Protocol: Weigh and record each pill. Warm all solutions to 37° C. Fill each chamber with 1 L simulated gastric fluid. Collect 1 ml of solution and mark as "0". Collect 1 ml of solution at 5 minutes, 10 minutes, 15 minutes, 30 minutes, 45 minutes and 60 minutes. Pour out SGF and keep pill in the chamber. Add 1 L of simulated intestinal fluid into the chamber. At 90 minutes (30 minute time point of the SIF solution) and 120 minutes, collect 1 ml of SIF solution. For every hour here after, collect 1 ml of solution until 8 hour mark reached in the total experiment. As such, time points for collection are 3, 4, 5, 6, 7, and 8 hours. All aliquots are frozen until ready for high pressure liquid chromatography.

The composition of the pills is adjusted as necessary. The viscosity of the HPMC may be adjusted as needed, in particular if less viscous HPMC is needed.

Animal Testing:

The tested pills included 1) Hydrocodone only; 2) Optimized tablet with hydrocodone, doxapram, and extended release doxapram; 3) Doxapram immediate release only; 4) Doxapram immediate release and extended release; 5) Doxapram extended release only; and 6) Control—no pill. The approximate dosages were 0.071 mg/kg to 5 mg/70 kg for Hydrocodone and 4.3 mg/kg to 300 mg/70 kg of Doxapram.

Nocioception Experiments:

Depending on the size of the tablets, either mice or rats are used. Mice are preferred because they don't learn as quickly as rats. If rats are used, each individual rat may be used once or twice before their pain responses are not accurate.

Protocol for Nociception Hot/Cold Experiments:

A hot/cold plate will be set to 52.5° C. (rats), 55° C. (mice), or 0° C. and allow the plate to reach that temperature. Animals will then be feed test or control the tablet. When the animal swallows/eats the tablet, it will be placed on the plate and a time will be recorded using a stopwatch. The time that the animal licks hind paws, jumps, shows agitated behavior, or vocalizes will be marked. Paw lick will be chosen as the time of nocioception for the studies but agitated behavior or vocalization will be chosen as an endpoint and marked as such. If nothing happens, the cut off time for mice will be 30 seconds and for rats will be 40 seconds. This will be marked as well, that cut off time was reached without any reaction. The cut off time will be utilized to prevent significant injury to the animal. At least one cold and one hot plate test will be performed on each animal. It may be beneficial to perform two sets of each for each animal. The animal will have a rest period of 1 hour minimum between each nociception test.

Plethsymography:

Run experiments with the pill inventory as listed above, 4 animals per group. Incrementally increase the number of pills given for groups 1 and 2 until LD50 reach. After 4 pills, and LD50 not reached, may need to change tablet formulation to include more hydrocodone per pill or give animals separate hydrocodone pills. Protocol: animal will be placed in a chamber and allow to acclimate for 5 to 10 minutes. Animals will then be give tablets/pills. Once the animal has swallowed the tablets/pills, the time will be mark as time 0 and the recordings will begin. The record will be recorded for 8 hours, and may adjust down to 6 hours.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any nonclaimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method for treating opioid abuse comprising administering a pharmaceutical composition comprising oxycodone for the treatment of pain and doxapram to a patient orally in a single dosage form, wherein the ratio of the amount of oxycodone to the amount of doxapram ranges from 1:100 w/w to 100:1 w/w.

2. The method of claim 1, wherein the single oral dosage form is a tablet, a syrup, a caplet, a gelcap, a lozenge or a capsule.

3. The method of claim 2, wherein the oral dosage form is a layered tablet.

4. The method of claim 1, wherein the doxapram is 1-ethyl-4-[2-(4-morpholinyl)ethyl]-3,3-diphenyl-2-pyrrolidinone monohydrochloride, monohydrate.

5. The method of claim 1, wherein the peak plasma concentration of doxapram ranges from about 1 μg/ml to 50 μg/ml.

6. The method of claim 1, wherein the peak plasma concentration of doxapram ranges from about 1 μg/ml to about 5 μg/ml.

7. The method of claim 1, wherein the peak plasma concentration of doxapram is at least 0.25 μg/ml.

8. The method of claim 1, wherein oxycodone is oxycodone hydrochloride ((5α)4,5-Epoxy-14-hydroxy-3-methoxy-17-methylmorphinan-6-one hydrochloride).

9. The method of claim 1, wherein the wherein the effective plasma oxycodone concentration is at least 1 μg/ml.

10. The method of claim 1, wherein the wherein the effective plasma oxycodone concentration is at least 5 μg/ml.

11. The method of claim 1, wherein the dose of oxycodone in the single dose formulation is 0.25 mg to 50 mg.

12. The method of claim 1, where the doxapram is selected from a racemic mixture, the (+) enantiomer (GAL-054), the (−) enantiomer (GAL-053), or mixtures thereof.

13. The method of claim 1, wherein the oxycodone and doxapram are formulated in different amounts to have a different ratio of oxycodone to doxapram by weight.

* * * * *